United States Patent
Mason et al.

(10) Patent No.: US 6,468,737 B1
(45) Date of Patent: Oct. 22, 2002

(54) IDENTIFICATION OF A NOVEL RETROVIRUS ASSOCIATED WITH PRIMARY BILIARY CIRRHOSIS AND AUTOIMMUNE DISORDERS

(75) Inventors: Andrew L. Mason, New Orleans, LA (US); Lizhe Xu, Metairie, LA (US); James Neuberger, Worcester (GB)

(73) Assignee: Alton Ochsner Medical Foundation, New Orleans, LA (US)

( * ) Notice: Subject to any disclaimer, the term of this patent is extended or adjusted under 35 U.S.C. 154(b) by 0 days.

(21) Appl. No.: 09/585,651

(22) Filed: Jun. 1, 2000

Related U.S. Application Data
(60) Provisional application No. 60/136,960, filed on Jun. 1, 1999.

(51) Int. Cl.$^7$ ............................ C12Q 1/70; C07H 21/04
(52) U.S. Cl. ........................................ 435/5; 536/23.72
(58) Field of Search ............................ 435/5; 536/23.72

(56) References Cited

PUBLICATIONS

Xu L. et al. Oct. 1998 A human retrovirus as a candidate gene in primary bilary cirrhosis. Heptology vol. 28 No. 4, part 2, p. 650A.
Mason et al. Oct. 1999. Retrovirus in autoimmune liver disease: genetic or environmental agents? Archivum Immunologiae et therapiae experimentalis. vol. 47, No. 5 pp. 291–292.
Alarcon–Segovia et al., 1973, "Features of Sjogren's syndrome in primary biliary cirrhosis", Ann Intern Med 79(1):31–6.
Burroughs et al., 1984, "Bacteriuria and primary biliary cirrhosis", Gut 25(2):133–7.
Epstein et al., 1980, "Primary biliary cirrhosis is a dry gland syndrome with features of chronic graft–versus–host disease", Lancet 1(8179):1166–8.
Gershwin et al., 1992, Molecular biology of the 2–oxo–acid dehydrogenase complexes and anti–microbial antibodies (W.B. Saunders, Philadelphia).
Joplin et al., 1992, "Membrane dihydrolipoamide acetyltransferase (E2) on human biliary epithelial cells in primary biliary cirrhosis", Lancet 339(8785):93–4.
Joplin et al., 1991, "Distribution of dihydrolipoamide acetyltransferase (E2) in the liver and portal lymph nodes of patients with primary biliary cirrhosis: an immunohistochemical study", Hepatology 14(3):442–7.
Neuberger, 1997, "Primary biliary cirrhosis", Lancet 350(9081):875–9.

(List continued on next page.)

Primary Examiner—Hankyel T. Park
(74) Attorney, Agent, or Firm—Pennie & Edmonds LLP

(57) ABSTRACT

The present invention relates, first, to the discovery, identification, and characterization of novel nucleic acid molecules, that are associated with PBC, Sjögren's syndrome, scleroderma, SLE, autoimmune thyroiditis and various other connective tissue disorders. The novel nucleotide sequences of the present invention are retroviral in origin and are indicative of a PBC retrovirus which bears a strong correlation with PBC. The present invention is based, in part, on the Applicant's data which is the first evidence to suggest that PBC patient's tissue may harbor a transmissible agent. The association of a retroviral infectious agent with PBC was first demonstrated by Applicants in vitro by co-culture of periportal lymph nodes derived from patients at time of transplantation and healthy biliary epithelium cells. The Applicant's discoveries as described herein, report the characterization of PBC-associated infectious agent as retroviral as demonstrated by electron microscopy and immunoblot reactivity. In addition, Applicants have characterized novel nucleotide sequences which are associated with the PBC-associated retrovirus.

8 Claims, 7 Drawing Sheets

OTHER PUBLICATIONS

Figure 1A:
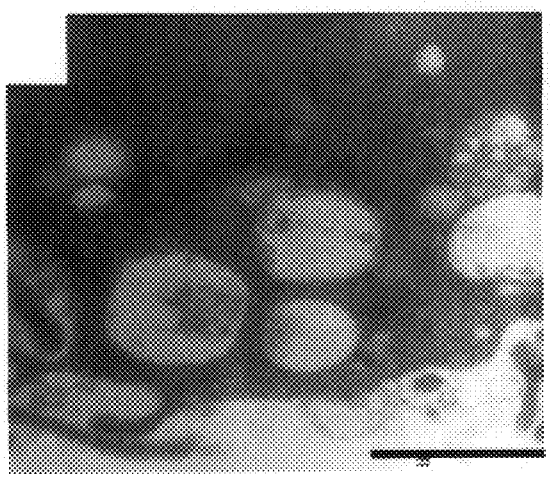

Neuberger et al., "Recurrence of primary biliary cirrhosis after liver transplantation", N Engl J Med 306(1):1–4.

O'Donohue et al., 1994, "Antibodies to atypical mycobacteria in primary biliary cirrhosis", J Hepatol 21(5):887–9.

Rubin et al., 1965, Primary Biliary Cirrhosis, Am J Pathol 46:387–407.

Sherlock et al., 1993, Primary biliary cirrhosis: definition and epidemiological features (Kluwer Academic Publishers, Boston) pp.341–349.

Stemerowicz et al., 1988, "Are antimitochondrial antibodies in primary biliary cirrhosis induced by R(rough)–mutants of enterobacteriaceae", Lancet 2(8621):1166–70.

Triger, 1980, "Primary biliary cirrhosis: an epidemiological study", Br Med J 281:772–775.

Tsuneyama et al., 1994, "Human combinatorial autoantibodies and mouse monoclonal antibodies to PDC–E2 produce abnormal apical staining of salivary glands in patients with coexistrent primary biliary cirrhosis and Sjogren's Syndrome", Hepatology 20(4 Pt 1):893–8.

Van de Water et al., 1989, "Detection of autoantibodies to recombinant mitochondrial proteins in patients with primary biliary cirrhosis", N Engl J Med 320(21):1377–80.

Van de Water et al., 1993, "Molecular mimicry in primary biliary cirrhosis. Evidence for biliary epithelial expression of a molecule cross–reactive with pyruvate dehydrogenase complex–E2", J Clin Invest 91(6):2653–64.

Wolke et al., 1984, "Malignancy in primary biliary cirrhosis. High incidence of breast cancer in affected women", Am J Med 76(6):1075–8.

FIG.3

IDENTIFICATION OF A NOVEL RETROVIRUS ASSOCIATED WITH PRIMARY BILIARY CIRRHOSIS AND AUTOIMMUNE DISORDERS

This application claims the benefit of the earlier filing date of provisional application No. 60/136,960, filed on Jun. 1, 1999, pursuant to 35 U.S.C. §119(e) and hereby incorporates said provisional application by reference.

1. INTRODUCTION

The present invention relates first, to the identification of a novel human retrovirus and the novel nucleotide sequences encoding a retroviral long terminal repeat and reverse transcriptase nucleotides associated with the existence of primary biliary cirrhosis (PBC), and other immune disorders such as Sjögren's syndrome, scleroderma, systemic lupus erythematosus (SLE), autoimmune thyroiditis and various other connective tissue disorders, in addition to lymphoma and breast cancer. The present invention further relates to methods for using the PBC retroviral nucleotides for the detection of PBC, Sjögren's syndrome, scleroderma, SLE, autoimmune thyroiditis and various other connective tissue disorders in patient samples. The present invention also relates to methods for using and targeting the PBC retroviral long terminal repeat and reverse transcriptase nucleotides in gene therapy protocols for the treatment of PBC, Sjögren's syndrome, scleroderma, SLE, autoimmune thyroiditis and various other connective tissue disorders in patients in need of such treatment. The present invention also relates to methods of treating or inhibiting PBC retroviral infection with antiviral agents, such as cytokines, inhibitors of reverse transcriptase, inhibitors of viral capping, and inhibitors of viral protease. The present invention further relates to diagnostic protocols and kits for the detection of PBC, Sjögren's syndrome, scleroderma, SLE, autoimmune thyroiditis and various other connective tissue disorders in tissue samples.

2. BACKGROUND OF THE INVENTION

Primary Biliary Cirrhosis and Autoimmunity

Primary biliary cirrhosis (PBC) is a progressive pluriglandular disease affecting the liver, pancreas, salivary and lachrymal glands (Neuberger, 1997, Lancet 850:875–79; Epstein et al., 1980, Lancet 1:1166–68). The hepatic disease is characterized by a florid bile duct lesion with lymphocytic infiltration and granulomatous destruction of 30 to 80 μm sized interlobular bile ducts (Rubin et al., 1965, Am. J. Pathol. 46:387–407). There is no curative therapy, apart from liver transplantation, and patients usually develop cirrhosis (Neuberger et al., 1997, Lancet 250:875–879). It is estimated to account for approximately 2% of patients dying from cirrhosis in Europe and 10% of patients that requiring orthotopic liver transplantation in North America (Neuberger et al., 1997, Lancet 250:875–879).

PBC is considered an archetypal autoimmune disease because patients have anti-mitochondrial antibodies (AMA) and can also present with other autoimmune disorders such as Sjögren's syndrome, scleroderma, systemic lupus erythematosus (SLE), autoimmune thyroiditis, and various other connective tissue disorders (Neuberger et al., 1997, Lancet 250:875–879). The clinical overlap with Sjögren's syndrome is particularly marked, as tests for xerophthalmia and xerostomia are positive in 70% to 100% of PBC patients (Alarcon-Segovia et al., 1973, Ann. Intern. Med. 79:31). In addition, patients with PBC have an increased incidence of urinary tract infection (Burroughs et al., 1984, Gut 25:133–7) and a 4 fold increased risk of breast cancer (Wolke et al., 1984, Am. J. Med. 76:1075).

The autoimmune phenomena associated with PBC have been well characterized. Over 95% of PBC patients have antibodies that bind and inhibit the dihydrolipoamide acetyltransferase enzymatic function of the E2 subunit of the pyruvate dehydrogenase complex (PDC) (Gershwin et al., 1992, Molecular biology of the 2-oxo-acid dehydrogenase complexes and anti-microbial antibodies. Philadelphia W. B. Saunders) These AMA have a higher affinity to the dehydrogenase E2 enzymes of mammals as compared to invertebrates and react to the E2 sub-units of other highly conserved inner membrane mitochondrial proteins of the oxoglutarate dehydrogenase complex, and branched chain 2-oxoacid dehydrogenase complex, and also the E1α and E1β sub-units of PDC. For patients with liver disease, reactivity to the E2 mitochondrial enzymes is specific to PBC but these AMA have been observed in individuals with Sjögren's syndrome and SLE as well (Van-de-Water et al., 1989, New Eng. J. Med. 320: 1377–80). The reason why PBC patients have an antigen driven immune response to human PDC-E2 may be partially explained by the findings of immunohistochemical studies. Using monoclonal and combinatorial AMA, PDC-E2 or antigens resembling PDC-E2 have been observed on the surface of cultured PBC biliary epithelium cells (Joplin et al., 1992, Lancet 339: 93–94), biliary epithelium and lymph node macrophages in PBC patient's tissues (Joplin et al., 1991, Hepatology 14: 442–447, Van-de-Water et al., 1993, J. Clin. Invest. 91: 2654–64), and salivary glands of patients with PBC and Sjögrens syndrome (Tsuneyama et al., 1994, Hepatology 20: 893–898). In essence, the tissues affected by the pluriglandular disease process are the same as those with the abnormal distribution of PDC-E2 antigens on epithelial cell surface.

The disease has been observed in all races and predominantly affects women (Neuberger, 1997, Lancet 350: 875–879). To date, non-HLA genetic factors predisposing to PBC have not been identified but a positive family history provides the greatest risk of developing disease (Sherlock et al., 1993, Primary biliary cirrhosis: definition and epidemiological features. Kluwer Academic Publishers, Doredrecht/Boston/London, pp. 341–49). There are well documented cases of clustering in families and one report documented a 2.4% familial prevalence (Sherlock et al., 1993, Primary biliary cirrhosis: definition and epidemiological features. Kluwer Academic Publishers, Doredrecht/Boston/London. 341–49 pp). No HLA class I alleles are associated with PBC but other immunogenetic factors appear to play an important role.

There are limited data to suggest an infectious etiology of PBC. The spread of disease has been documented in unrelated care providers and has also been associated with a particular water supply in Sheffield, England which was reconfirmed with a follow-up study 10 year later (Sherlock et al., 1993, Primary biliary cirrhosis: definition and epidemiological features. Kluwer Academic Publishers, Doredrecht/Boston/London. pp. 341–49, Trigger 1980, Br. Med. J. 281: 772–5). Although the data are subject to debate, the specific anti-mitochondrial antibodies associated with PBC have been detected in related and non-related family members (Sherlock et al., 1993, Primary biliary cirrhosis: definition and epidemiological features. Kluwer Academic Publishers, Doredrecht/Boston/London, 341–49). Further evidence for an infectious etiology of PBC is suggested by the observation of recurrent disease in the hepatic allograft of approximately 15% of PBC patients undergoing orthotopic liver transplantation. This evidence includes the observation of granulomatous destruction of bile ducts after liver transplantation, the continued presence of serum AMA in the majority of PBC patients (Trigger, 1980, Br. Med. J. 281: 772–5), and immunohistochemical evidence of PDH-E2 on biliary epithelial cell surface in the allograft (Neuberger et al., 1982, N. Eng. J. Med. 306: 1–4).

The epidemiology of PBC does not suggest a simple infectious disease pattern. If an infectious etiology is entertained, it is probable that infection only causes PBC in predisposed individuals due to the modulating effects of genetic, hormonal, and environmental factors. This may partially explain why PBC patients develop AMA and liver disease while other family members develop merely develop serum AMA reactivity without PBC. Many investigators have postulated that either mycobacteria, or enterobacterial R-forms are etiologically related to PBC as they have the highly conserved dehydrogenase enzymes which possibly induce autoimmunity by the mechanism of microbial molecular mimicry with host proteins (O'Donohue et al., 1994, J. Hepatol. 21: 887–889; Stemerowicz et al., 1988, Lancet 1: 1166–1170). Others have made the claim that recurrent bacterial urinary tract infections may be the source of such antigen exposure (Burroughs et al., 1984, Gut 25: 133–7), but this hypothesis provides no explanation for limited disease restricted to biliary epithelium with an immune response to a ubiquitous autoantigen. Thus, the involvement of an infectious agent with PBC still remains to be characterized.

3. SUMMARY OF THE INVENTION

The present invention relates, first, to the discovery, identification, and characterization of novel nucleic acid molecules, that are associated with PBC. The novel nucleotide sequences of the present invention are retroviral in origin and are indicative of a PBC retrovirus which bears a strong correlation with PBC. The present invention is based, in part, on the Applicants' data which is the first evidence to suggest that PBC patient's tissue may harbor a transmissible agent. The association of a retroviral infectious agent with PBC was first demonstrated by Applicants in vitro by co-culture of periportal lymph nodes derived from patients at time of transplantation and healthy biliary epithelium cells. The Applicants' discoveries as described herein, report the characterization of PBC-associated infectious agent as retroviral as demonstrated by electron microscopy and immunoblot reactivity. In addition, Applicants have characterized novel nucleotide sequences which are associated with the PBC-associated retrovirus.

The present invention encompasses nucleic acid molecules which comprise the following nucleotide sequences: (a) nucleotide sequences comprising the PBC retroviral sequences disclosed herein; and (b) nucleotide sequences that encompass portions or fragments of the PBC retroviral nucleotides which can be utilized as probes or primers in the methods of the invention for identifying and diagnosing individuals at a risk for, or exhibiting PBC, Sjögren's syndrome, scleroderma, SLE, autoimmune thyroiditis, various other connective tissue disorders and lymphoma.

The invention also encompasses the expression products of the nucleic acids molecules listed above; i.e., proteins and/or polypeptides that are encoded by the above PBC retroviral nucleic acid molecules, or by degenerative, e.g., allelic variants thereof.

The compositions of the present invention further encompass antagonists of the PBC retroviral gene products, including small molecules, large molecules, and antibodies, as well as nucleotide sequences that can be used to inhibit PBC retroviral gene expression, e.g., antisense, ribozyme molecules, and gene or regulatory sequence replacement constructs.

The present invention relates to therapeutic methods and compositions for treatment and prevention of diseases and disorders associated with the presence of the PBC retroviral nucleotides, including but not limited to, PBC, Sjögren's syndrome, scleroderma, SLE, autoimmune thyroiditis and various other connective tissue disorders. The therapeutic methods and compositions of the present invention are designed to target the PBC retroviral nucleotides, such as antisense molecules and ribozymes. The therapeutic methods and compositions of the present invention are also designed to target PBC retroviral gene products, including small molecules, large molecules, and antibodies. The present invention further relates to the vaccine formulations based on isolated PBC associated virus particles in an attenuated form and/or PBC retroviral gene products for the treatment and/or prevention of disorders associated with the presence of PBC retroviral nucleotides.

In addition, the present invention is directed to methods that utilize the nucleotide sequences of the present invention for the diagnostic evaluation, genetic testing and prognosis of PBC retroviral infection and/or associated disorders including, (but not limited to PBC, Sjögren's syndrome, scleroderma, SLE, autoimmune thyroiditis and various other connective tissue disorders. For example, in one embodiment, the invention relates to methods of diagnosing PBC retroviral infection and/or associated disorders, wherein such methods comprise measuring PBC retroviral gene expression in a patient sample suspected of exhibiting such a disorder. In one embodiment, nucleic acid molecules of the present invention can be used as primers for diagnostic PCR analysis for the identification of PBC retroviral nucleotides which correlate with the presence of a PBC retrovirus and/or associated disorders PBC, Sjögren's syndrome, scleroderma, SLE, autoimmune thyroiditis, various other connective tissue disorders and lymphoma. In yet another embodiment, the nucleic acid molecules of the present invention may be used to detect breast cancer in a subject shown also to be infected with PBC retrovirus in tissue samples other than breast tissue e.g., liver tissue or serum. In another embodiment, antibodies or serologic assays may be used to detect breast cancer in a subject shown to be also infected with PBC in tissue samples other than breast tissue, e.g., liver tissue or serum samples. In yet another embodiment, nucleic acid molecules of the present invention can be used as primers for therapeutic PCR analysis in order to monitor the presence of a PBC retrovirus in order to determine the effectiveness of a therapeutic protocol.

In yet another embodiment, the present invention relates to diagnostic evaluation and prognosis methods which are based on immuno reactivity of a patient sample to PBC-specific antibodies. In this embodiment, isolated serum from a PBC-positive patient, monoclonal antibodies or polyclonal antibodies having specificity for PBC-associated virus may be used to detect PBC-associated retrovirus in a patient sample as a method of diagnosis or as a method of determining the effectiveness of a therapeutic protocol.

In yet another embodiment, the present invention relates to methods of treating individual, infected with PBC retrovirus. In particular, the present invention relates to combinations of antiviral and immunomodulation therapy to control viral replication and disease symptoms in individuals infected with PBC retrovirus the present invention further relates to vaccines and other prophylectic treatments to prevent disease in genetically susceptible individuals.

3.1 Definitions

"Complement" or "tag complement" as used herein in reference to oligonucleotide tags refers to an oligonucleotide to which a oligonucleotide tag specifically hybridizes to form a perfectly matched duplex or triplex. In embodiments where specific hybridization results in a triplex, the oligonucleotide tag may be selected to be either double stranded or single stranded. Thus, where triplexes are formed, the term "complement" is meant to encompass either a double stranded complement of a single stranded oligonucleotide tag or a single stranded complement of a double stranded oligonucleotide tag.

The term "oligonucleotide" as used herein includes linear oligomers of natural or modified monomers or linkages, including deoxyribonucleosides, ribonucleosides, a-anomeric forms thereof, peptide nucleic acids (PNAs), and the like, that are capable of specifically binding to a target polynucleotide. The specific binding is determined by way of a regular pattern of monomer-to-monomer interactions, such as Watson-Crick type of base pairing, base stacking, Hoogsteen or reverse Hoogsteen types of base pairing, or the like. Usually monomers are linked by phosphodiester bonds or analogs thereof to form oligonucleotides that range in size from a few monomeric units, e.g. 3–4, to several tens of monomeric units. Whenever an oligonucleotide is represented by a sequence of letters, such as "ATGCCTG," it will be understood that the nucleotides are in 5'>3' order from left to right and that "A" denotes deoxyadenosine, "C" denotes deoxycytidine, "G" denotes deoxyguanosine, and "T" denotes thymidine, unless otherwise noted. Analogs of phosphodiester linkages include phosphorothioate, phosphorodithioate, phosphoranilidate, phosphoramidate, and the like. It is clear to those skilled in the art when oligonucleotides having natural or non-natural nucleotides may be employed, e.g. where processing by enzymes is called for, usually oligonucleotides consisting of natural nucleotides are required. "Perfectly matched" in reference to a duplex means that the poly- or oligonucleotide strands making up the duplex form a double stranded structure with one other such that every nucleotide in each strand undergoes Watson-Crick basepairing with a nucleotide in the other strand. The term also comprehends the pairing of nucleoside analogs, such as deoxyinosine, nucleosides with 2-aminopurine bases, and the like, that may be employed. In reference to a triplex, the term means that the triplex consists of a perfectly matched duplex and a third strand in which every nucleotide undergoes Hoogsteen or reverse Hoogsteen association with a basepair of the perfectly matched duplex. Conversely, a "mismatch" in a duplex between a tag and an oligonucleotide means that a pair or triplet of nucleotides in the duplex or triplex fails to undergo Watson-Crick and/or Hoogsteen and/or reverse Hoogsteen bonding. It also includes known types of modifications, for example, labels which are known in the art, methylation, "caps", substitution of one or more of the naturally occurring nucleotides with an analog, internucleotide modifications such as, for example, those with uncharged linkages (e.g., methyl phosphonates, phosphotriesters, phosphoamidates, carbamates, etc.) and with charged linkages (e.g., phosphorothioates, phosphorodithioates, etc.), those containing pendant moieties, such as, for example proteins (including for e.g., nucleases, toxins, antibodies, signal peptides, poly-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide.

As used herein, "nucleoside" includes the natural nucleosides, including 2'-deoxy and 2'-hydroxyl forms, e.g. as described in Kornberg and Baker, DNA Replication, 2nd Ed. (Freeman, San Francisco, 1992). "Analogs" in reference to nucleosides includes synthetic nucleosides having modified base moieties and/or modified sugar moieties, e.g. described by Scheit, Nucleotide Analogs (John Wiley, New York, 1980); Uhlman and Peyman, Chemical Reviews, 90: 543–584 (1990), or the like, with the only proviso that they are capable of hybridization. Such analogs include synthetic nucleosides designed to enhance binding properties, reduce degeneracy, increase or decrease specificity, and the like.

As used herein, a polynucleotide "derived from" a designated sequence refers to a subset of the designated sequence of approximately at least about 6 nucleotides, preferably at least about 8 nucleotides, more preferably at least about 10–12 nucleotides, and even more preferably at least about 15–20 nucleotides. "Corresponding" means homologous to or complementary to the designated sequence. Preferably, the sequence of the region from which the polynucleotide is derived is homologous to or complementary to a sequence which is unique to an PBC associated viral genome. More preferably, the derived sequence is homologous or complementary to a sequence that is unique to all or to a majority of PBC associated viral isolates. Whether or not a sequence is unique to the a PBC associated viral genome can be determined by techniques known to those of skill in the art. For example, the sequence can be compared to sequences in databanks, e.g., Genebank, to determine whether it is present in the uninfected host or other organisms. The sequence can also be compared to the known sequences of other viral agents, including retroviruses. The correspondence or non-correspondence of the derived sequence to other sequences can also be determined by hybridization under the appropriate stringency conditions. Hybridization techniques for determining the complementarity of nucleic acid sequences are known in the art, and are discussed infra. See also, for example, Maniatis et al. (1982). In addition, mismatches of duplex polynucleotides formed by hybridization can be determined by known techniques, including for example, digestion with a nuclease such as S1 that specifically digests single-stranded areas in duplex polynucleotides. Regions from which typical DNA sequences may be "derived" include but are not limited to, for example, regions encoding specific epitopes, as well as non-transcribed and/or non-translated regions.

The derived polynucleotide is not necessarily physically derived from the nucleotide sequence shown, but may be generated in any manner, including for example, chemical synthesis or DNA replication or reverse transcription or transcription. In addition, combinations of regions corresponding to that of the designated sequence may be modified in ways known in the art to be consistent with an intended use.

The term "recombinant polynucleotide" as used herein intends a polynucleotide of genomic, cDNA, semisynthetic, or synthetic origin. The term further intends that the polynucleotide (1) is not associated with all or a portion of a polynucleotide with which it is associated in nature; (2) is linked to a polynucleotide other than that to which it is linked in nature; or (3) does not occur in nature.

As used herein, the "sense strand" of a nucleic acid contains the sequence that has sequence homology to that of mRNA. The "anti-sense strand" contains a sequence which is complementary to that of the "sense strand".

The term "primer" as used herein refers to an oligomer which is capable of acting as a point of initiation of synthesis of a polynucleotide strand when placed under appropriate conditions. The primer will be completely or substantially complementary to a region of the polynucleotide strand to be copied. Thus, under conditions conducive to hybridization, the primer will anneal to the complementary region of the analyte strand. Upon addition of suitable reactants, (e.g., a polymerase, nucleotide triphosphates, and the like), the primer is extended by the polymerizing agent to form a copy of the analyte strand. The primer may be single-stranded, or alternatively may be partially or fully double-stranded.

The terms "analyte polynucleotide" and "analyte strand" refer to a single- or double-stranded nucleic acid molecule which is suspected of containing a target sequence, and which may be present in a biological sample. As used herein, the term "oligomer" refers to primers and to probes. The term oligomer does not connote the size of the molecule.

As used herein, the term "probe" refers to a structure comprised of a polynucleotide which forms a hybrid structure with a target sequence, due to complementarity of at least one sequence in the probe with a sequence in the target region. The polynucleotide regions of probes may be composed of DNA, and/or RNA, and/or synthetic nucleotide analogs. Included within probes are "capture probes" and "label probes". Preferably the probe does not contain a sequence complementary to sequence(s) used to prime the polymerase chain reaction (PCR).

As used herein, the term "target region" refers to a region of the nucleic acid which is to be amplified and/or detected. The term "target sequence" refers to a sequence with which a probe or primer will form a stable hybrid under desired conditions.

As used herein, the term "viral RNA", which includes PBC associated RNA, refers to RNA from the viral genome, fragments thereof, transcripts thereof, and mutant sequences derived therefrom.

As used herein, a "biological sample" refers to a sample of tissue or fluid isolated from an individual. Thus, "biological sample", includes but is not limited to, for example, plasma, serum, spinal fluid, lymph fluid, the external sections of the skin, respiratory, intestinal, and genitourinary tracts, tears, saliva, milk, blood cells, tumors, organs, and also samples of in vitro cell culture constituents (including but not limited to conditioned medium resulting from the growth of cells in cell culture medium, putatively virally infected cells, recombinant cells, and cell components).

4. DETAILED DESCRIPTION OF THE DRAWINGS

Figure 1B:
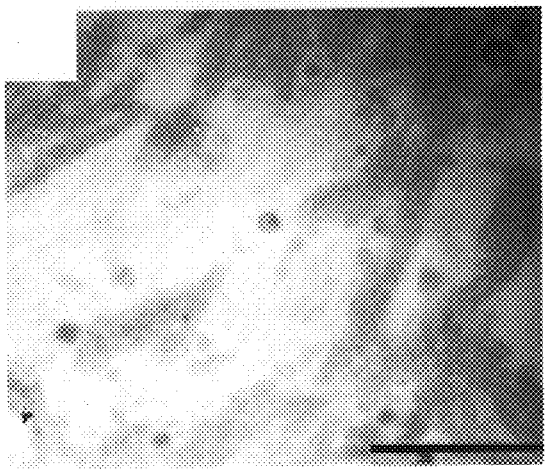
Figure 2A:
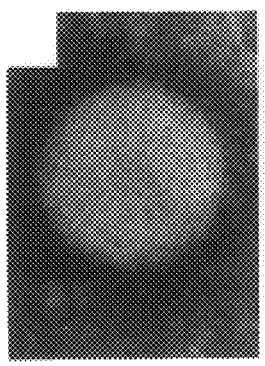
Figure 2B:
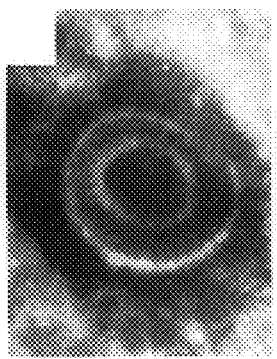
Figure 2C:
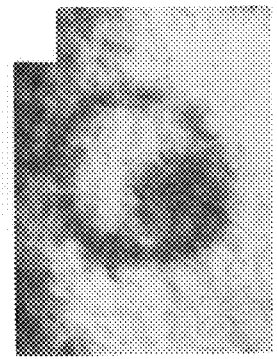
Figure 2D:
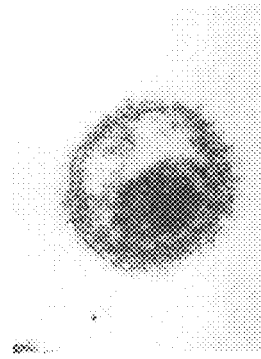

FIG. 1 Electron micrographs of biliary epithelial cells derived from PBC patients showing virus-like particles with a dense oval nuclear core (a and b: white bar represents 1 $\mu$m; inset 5× magnification of micrographs).

FIG. 2 Electron micrographs of particles with morphology similar to MMTV. Panels (a) and (b) show negatively stained virus-like particles from the supernatant of PBC co-culture studies. Panel (a) reveals a round particle with external envelope glycoprotein "spikes". Panel (b) shows a particle where the negative stain has penetrated the envelope to reveal an eccentrically located icosohedral core. Both (a) and (b) are comparable to (c) showing an enlarged particle from FIG. 1a; as well as (d) the prototypical B-type particle MMTV.

Figure 3:
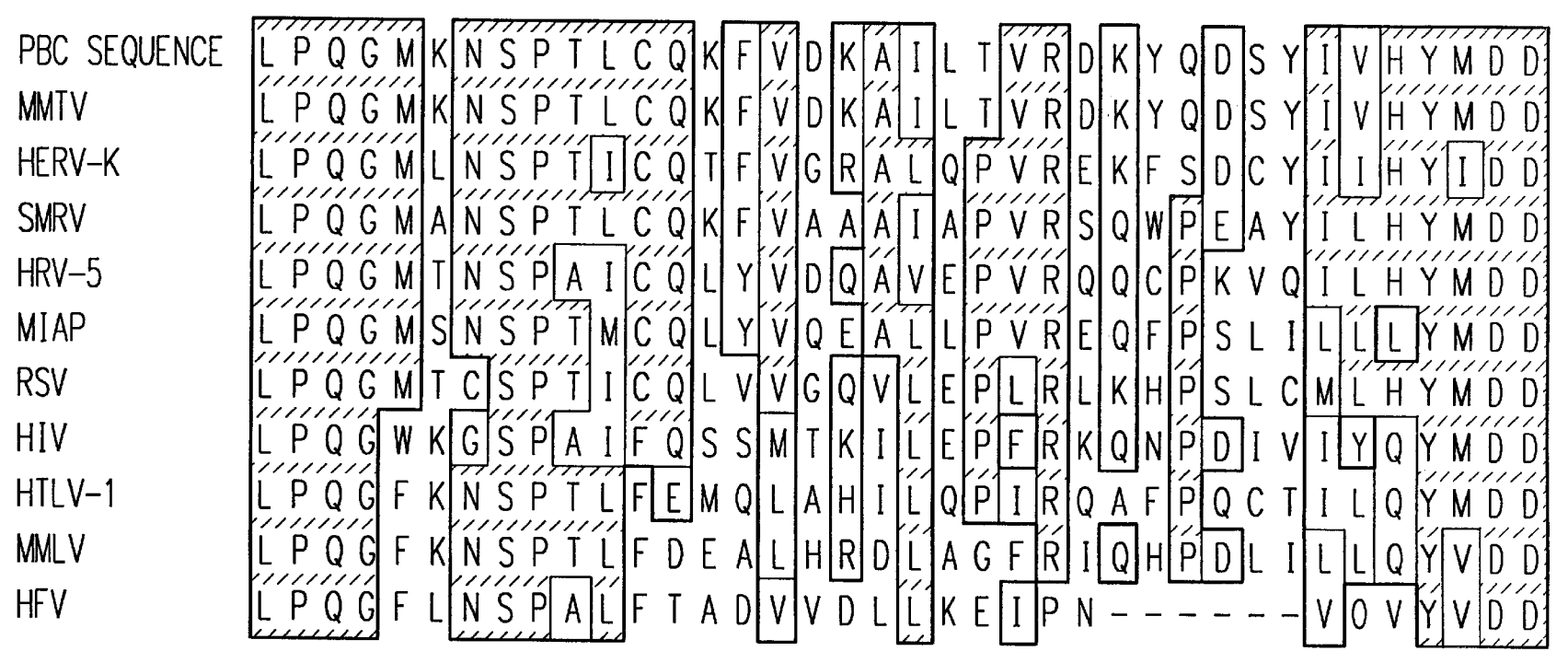

FIG. 3 Pylogenetic tree of Clustal W alignment of human retroviral reverse transcriptase pol gene sequences demonstrating closest homology to the PBC-related retrovirals with HERV-K10 and HRV-5 related to B and D type retroviruses. PBC-RV PBC retroviral related HERV-K10 human endogenous retrovirus K10; HRV-5 human retrovirus 5, HIV Human immunodeficiency virus, MSRV Multiple sclerosis retrovirus, HTLV1 Human T-cell leukemia virus-1, HFV human foamy virus, HBV hepatitis B virus.

Figure 4A:
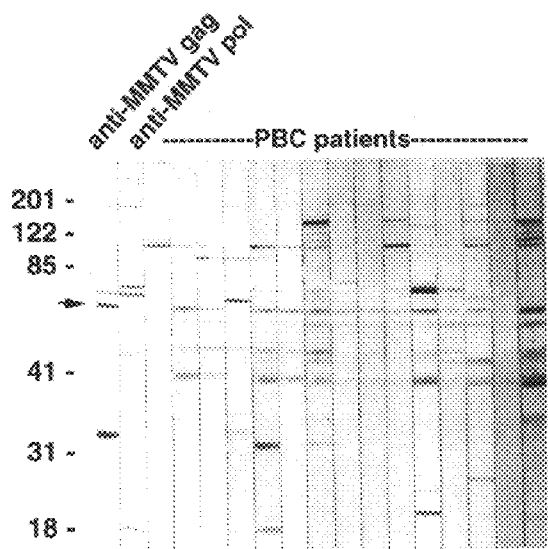
Figure 4B:
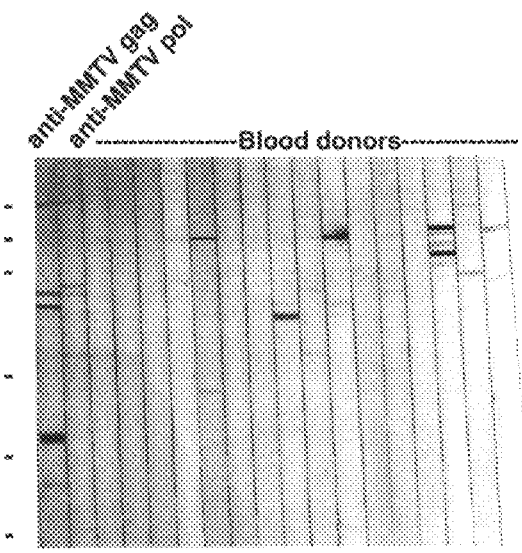

FIG. 4 MMTV protein Western blot studies performed with cell lysates from MM5MT cell line developed with serum from PBC patients and blood donors. Polyclonal positive controls to MMTV gag and pol (NCI).

Figure 5A:
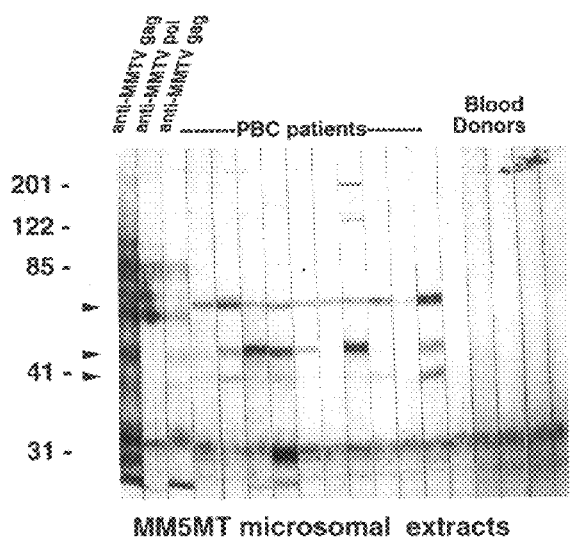
Figure 5B:
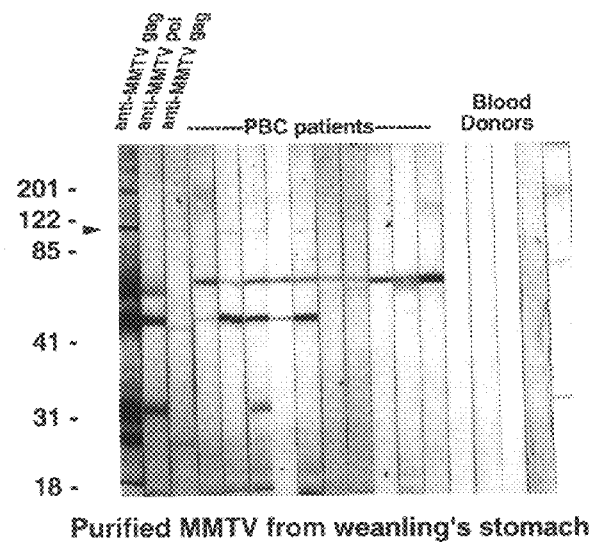

FIG. 5 MMTV Western blot studies with microsomal extracts from MM5MT or purified virus. Positive controls as in FIG. 4 with monoclonal anti-MMTV p27 gag.

Figure 6A:
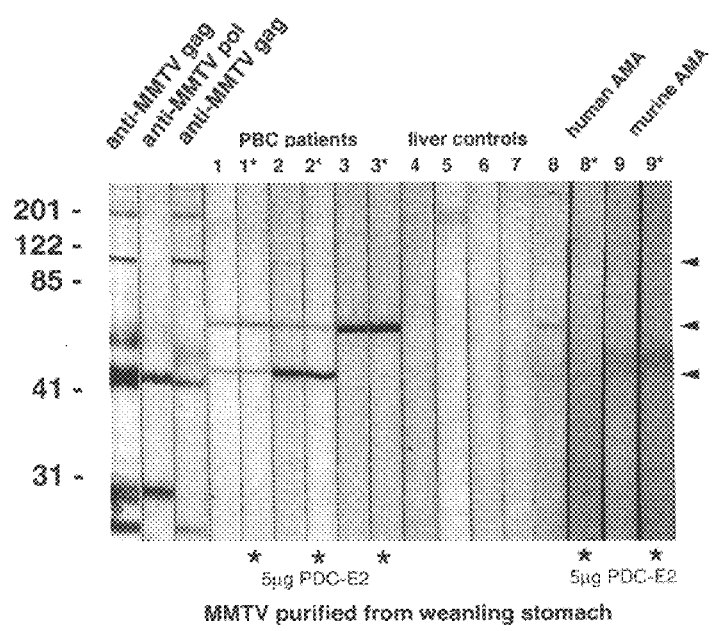
Figure 6B:
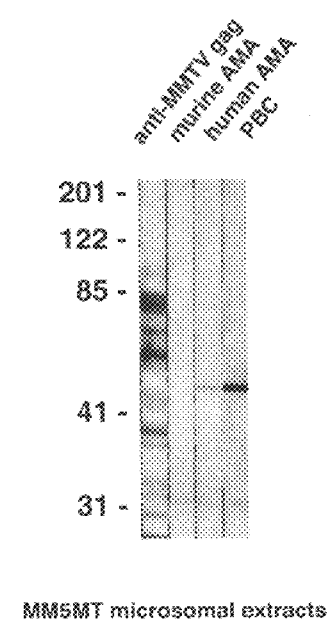

FIG. 6 MMTV protein Western blot studies performed with purified MMTV and MM5MT microsomal extracts developed with serum from PBC and liver disease patients as well as eluted human AMA from PBC serum and murine monoclonal AMA. No 50 kDa or 70 kDa reactivity was seen with murine AMA. Preincubation with PDC-E2 diminished the human AMA reactivity but had little effect on PBC patient serum reactivity.

FIG. 7 AMA immunohistochemical study of normal BEC incubated with PBC lymph nodes for 7 days. The electron micrographs demonstrate AMA reactivity to hollow structures on the cell surface. The arrow points to a particle within a vesicle typical of an intracisternal A-type particle (white bar=500 nm; magnification a>b).

5. DETAILED DESCRIPTION OF THE INVENTION

The present invention is based on the discovery, identification and characterization of a PBC retrovirus isolated from tissue samples of patients with PBC. An isolated preparation of virus was obtained from liver and skin samples of patients with PBC. Once the virus was isolated, total RNA was extracted and converted to cDNA using random primers and reverse transcriptase. A hereto for unidentified novel exogenous human retroviral sequence was amplified from the patient's tissue sample.

The present invention relates to isolated preparations of a novel human retrovirus associated with PBC, herein referred to as "PBC retrovirus". The present invention relates to isolated genome of the novel human retrovirus and the nucleotide and the nucleic acid molecules encoding said genome. The present invention relates to nucleotide sequences that encompass portions or fragments of the PBC retroviral nucleotides which can be utilized as probes or primers in the methods of the invention for identifying and diagnosing individuals at a risk for or exhibiting PBC, Sjögren's syndrome, scleroderma, SLE, autoimmune thyroiditis and various other connective tissue disorders.

The present invention encompasses methods for the diagnostic evaluation, and prognostic evaluation of PBC retroviral infection and associated disorders including PBC, Sjögren's syndrome, scleroderma, SLE, autoimmune thyroiditis and various other connective tissue disorders. In one embodiment, these methods comprise utilizing the nucleic acid molecules of the present invention to measure levels of PBC retroviral nucleotide sequences. In yet another embodiment, these methods comprise utilizing serum, polyclonal or monoclonal antibodies which are specific for PBC retrovirus to measure levels of the PBC virus and/or viral proteins in a patient's sample.

The present invention further provides for diagnostic kits for the practice of such methods.

The present invention relates to therapeutic methods and compositions for treatment and prevention of diseases and disorders related to the infection with the PBC retrovirus and/or presence of the PBC retroviral nucleotide sequences, including but not limited to, PBC, Sjögren's syndrome, scleroderma, SLE, autoimmune thyroiditis and various other connective tissue disorders. The therapeutic methods and compositions are designed to target the PBC retroviral nucleotides, such as antisense molecules, and ribozymes. The therapeutic methods and compositions of the present invention are also designed to target the PBC retroviral gene products, including small molecules, large molecules and antibodies. In particular, the present invention encompasses the use of the isolated PBC retrovirus and retroviral gene products to generate antibodies for the detection of the PBC retrovirus in tissue samples in diagnostic protocols and/or for formulation into vaccine preparations for the treatment and/or prevention of PBC retrovirus infection and related disorders, PBC, Sjögren's syndrome, scleroderma, SLE, autoimmune thyroiditis, various other connective tissue disorders, lymphoma and breast cancer.

5.1 PBC Retroviral Nucleotides

The retroviral nucleotides of the present invention are described herein. Unless otherwise stated, the term 'retroviral or viral nucleotides or nucleic acid molecules' refers collectively to the sequences described herein. The novel human retroviral nucleotides of the present invention include, but are not limited to, (a) novel clones identified in samples from PBC patents:

The following clone was isolated from a BEC cDNA library obtained from three patients with PBC.

Clone 1 pol
TAACGGCCGCCAGTGTGCTGGAATTCTG-
CAGATTGGAAGGTGTTGCCACAGGGTAT-
GAAAAATAGCCCTACTTTATGTCAAAAAT TTGTA-
GATAAAGCTATATTGACTGTAAGGGATAAATATC
AAGACTCATATATGTGCATTACATGGAT-
GACCTCCC (SEQ ID NO:1)

The following clone was isolated from a BEC cDNA library obtained from patients with PBC using oligonucleotide primers complementary to conserved nucleotide in the MMTV LTR and MMTV pol sequence.

Pol
CCCATAAGGTGAAAGGCAGTGTAGGGAT-
CACAAAGGGATGTATAATCCCTGATT-
TATCCTCATGTTGCCAGCGGAGTGGCT-
GACTACTACGCGCCACCCCACAGGCCATGCCTA
AACCTTGAAGAGAACTTTCAGTTTGGT-
GAATAGGCCAATTAGCTGGCCAGTCTCT-
GCCTGCTATACAAGTTTTATCTGCCCCG-
GTATCCAAGAGACCGAGGAATCTTCTTCCATTC
AAGGAAATATGAAGCATGGGTCTGGAAT-
CACTTATTTCCTGCACCCAATGTACAT-
GACTTGTTGATCCGAAGCCTTCTGAGC-
CTCGTTCTTCCTGATTACAGG (SEQ ID NO:2)

The following clones were obtained from bile samples of different patients with PBC.

T-CI-26 pol
TTGCCACAGGGTATGAAAAATAGC-
CCTACTTTATGTCAAAAATTTGTA-
GATAAAGCTATATTGACTGTAAGG-
GATAAATATCAAGACTCATATATGTGCATTACATG
GATGACCTCCCA (SEQ ID NO:3)

T-CI-31 pol
GTGCTGCCCCAGGGTATGAAAAATAGC-
CCTACTTTATGTCAAAAATTTGTA-
GATAAAGCTATATTGACTGTAAGG-
GATAAATATCAAGACTCATATATGTGCATTACAT
GGATGACCTAAGGGCGAATTCCAGCA-
CACTGCGCCGT (SEQ ID NO:4)

T-CI-30 pol
GTTGCCCCAGGGTATGGAAAAATAGC-
CCTACTTTATGTCAAAAATTTGTA-
GATAAAGCTATATAGACTGTAAGG-
GATAAATATCAAGACTCATATATGTGCATTACATG
GATGA (SEQ ID NO:5)

T-CI-29 pol
GCTACCACAAGGTATGAAAAATAGC-
CCTACTTTATGTCAAAAATTTGTA-
GATAAAGCTATATTGACTGTAAGGGATAAATAT
CAAGACTCATATATGTGCATTACATGGATGACAT
CCC (SEQ ID NO:6)

T-CI-28 pol
GTTACCACAGGGTATGAAAAATAGC-
CCTACTTTATGTCAAAAATTTGTA-
GATAAAGCTATATGACTGTAAGG-
GATAAATATCAAGACTCATATATGTGMTTACATGR
TAGACTCCCA (SEQ ID NO:7)

T-CI-27 pol
CTGCCACAAGGTAGGGAGGTCATCCATG-
TAATGCACAATATATGAGTCTTGATATT-
TATCCCTTACAGTCAATATAGCTTTATC-
TACAAATTTTTGACATAAAGTAGGGCTATTTTTC
ATACCCTGTGGCAGCACCTTCCAAA (SEQ ID NO:8)

The following clones were obtained from BEC cDNA libraries and bile samples of at least eight patients with PBC:

Es60-7/GO16 LTR
ACAGAAGAGCTATTAAAAGAGT-
CAAGGGTGAGAGCCCTGCGAGCACGAAC-
CGCAACTTCCCCCAATAGCCCCAG-
GCAAAGCAGAGCTATGCCAAGTTTGCAGCAGA
GAATGAATATGTCTTTATCTGATGGGCTCATCC
(SEQ ID NO:9)

Es60-6/GO16 LTR
ACAGAAGAGCTATTAAAAGAGT-
CAAGGGTGAGAGCCCTGCGAGCACGAAC-
CGCAACTTCCCCCAATAGCCCCAGGCAA AGCA-
GAGCTATGCCAAGTTTGCAGCAGAGAATGAAT
ATGTCTTTATCTGATGGGCTCATC (SEQ ID NO:10)

Es60-5/GO16 LTR
TGAGCCCATCAGACAAAGACATATTCAT-
TCTCTGCTGCAAACTTGGCATAGCTCT-
GCTTTGCCTGGGGCTATTGGGGGAAGT-
TGCGGTTCGTGCTCGCAGGGCTCTCACCCTTGA
CTCTTTTAATAGCTCTTCTGTGCAAGATTAC (SEQ ID NO:11)

Es60-4/GO16 LTR
TGAGCCCATCAGACAAAGACATATTCAT-
TCTCTGCTGCAAACTTGGCATAGCTCT-
GCTTTGCCTGGGGCTATTGGGGGAAGT-
TGCGGTTCGTGCTCGCAGGGCTCTCACCCTTGA
CTCTTTTAATAGCTCTTCTGTGCAAGATTAC (SEQ ID NO:12)

Es60-3/GO16 LTR
GCCAGTGTGATGGATATCTGCAGAAT-
TCGCCCTTTTGTTTCCCACCAAGGAC-
GACCCGTCTGCGCACAAACGGATGAGC-
CCATCAGACAAAGACATATCATTCTCTGCTGCA
AACTTGGCATAGCTCTGCTTTGC-
CTGGGGCTATTGGGGGA (SEQ ID NO:13)

Es60-2/GO16 LTR
ACAGAAGAGCTATTAAAAGAGT-
CAAGGGTGAGAGCCCCGCGAGCACGAAC-
CGCAACTTCCCCCAATAGCCCCAG-
GCAAAGCAGAGCTATGCCAAGTTTGCAGCAG
AGAATGAATATGTCTTTGTCTGATGGGCTCATCCG
(SEQ ID NO:14)

Es60-1/GO16 LTR
CGCCAGTGTGATGGATATCTGCAGAAT-
TCGCCCTTATGTTTCCCACCAAGGAC-

GACCCGTTTGCGCACAAACGATGAGC-
CCATCAGACAAAGACA (SEQ ID NO:15)

The PBC associated human retroviral nucleotide sequences of the present invention include: (a) nucleotide sequences and fragments thereof(e.g. SEQ ID Nos: 1, 2, 3, 4, 5, 6, 7, 8, 9, 10, 11, 12, 13, 14, or 15) that encode a portion of the PBC retroviral genome of the present invention; (b) nucleotide sequences that comprise SEQ ID NOS: 1, 2, 3, 4, 5, 6, 7, 8, 9, 10, 11, 12, 13, 14, or 15 that encode a PBC retroviral genome or a portion, mutant or allelic variant thereof; (c) nucleotide sequences comprising the novel human retroviral sequences disclosed herein that encode retroviral gene products, as well as fragments thereof; and (d) nucleotide sequences (e.g., primers) within SEQ ID NOS. 1, 2, 3, 4, 5, 6, 7, 8, 9, 10,11, 12, 13, 14, or 15), or a portion thereof, which can be utilized as part of the methods of the invention for identifying and diagnosing individuals at a risk for exhibiting PBC, Sjögren's syndrome, scleroderma, SLE, autoimmune thyroiditis and various other connective tissue disorders.

The PBC retroviral nucleotide sequences of the invention further include: (a) any nucleotide sequence that hybridizes to the complement of a nucleic acid molecule that encodes an PBC retroviral gene product under highly stringent conditions, e.g., hybridization to filter-bound DNA in 0.5 M NaHPO$_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3). In a preferred embodiment, such nucleic acid molecules encode gene products functionally equivalent to a PBC retroviral gene product; and (b) any nucleotide sequence that hybridizes to the complement of a nucleic acid molecule that encodes a PBC retroviral gene product under less stringent conditions, such as moderately stringent conditions, e.g., washing in 0.2×SSC/0.1% SDS at 42° C. (Ausubel et al., 1989, supra), and which encodes a functionally equivalent PBC retroviral gene product. The present invention relates to isolated nucleotide sequences obtained from a human, which are either endogenous or exogenous to the human genome.

Among the nucleic acid molecules of the invention are deoxyoligonucleotides ("oligos") which hybridize under highly or moderately stringent conditions to the PBC retroviral nucleic acid molecules described above. Exemplary highly stringent conditions may refer, e.g., to washing in 6×SSC/0.05% sodium pyrophosphate at 37° C. (for 14-base oligos), 48° C. (for 17-base oligos), 55° C. (for 20-base oligos), and 60° C. (for 23-base oligos). These nucleic acid molecules may encode or act as antisense molecules, useful, for example, in PBC retroviral gene regulation, and/or as antisense primers in amplification reactions of PBC retroviral gene nucleic acid sequences. Further, such sequences may be used as part of ribozyme and/or triple helix sequences, also useful for PBC retroviral gene regulation. Still further, such molecules may be used as components of diagnostic methods whereby, for example, the presence of a particular PBC retroviral nucleic acid molecules involved in a disorder, such as PBC, Sjögren's syndrome, scleroderma, SLE, autoimmune thyroiditis and various other connective tissue disorders may be detected.

Fragments of the PBC retroviral nucleic acid molecules can be at least 10 nucleotides in length. In alternative embodiments, the fragments can be about 20, 30, 40, 50, 60, 70, 80, 90, 100, 200, 300, 400, 500, 1000, or more nucleotides in length. Alternatively, the fragments can comprise sequences that encode at least 10, 20, 30, 40, 50, 100, or more continuous amino acid residues of the PBC retroviral gene products.

The PBC retroviral nucleotide sequences of the invention can be readily obtained, for example, by standard sequencing and the sequence provided herein.

With respect to the cloning of additional allelic variants of the PBC retroviral genome gene and homologues from other species (e.g., mouse), the isolated PBC retroviral gene sequences disclosed herein may be labeled and used to screen a cDNA library constructed from mRNA obtained from appropriate cells or tissues (e.g., brain and retinal tissues) derived from the organism (e.g., guinea pig, bovine, and mouse) of interest. The hybridization conditions used should generally be of a lower stringency when the cDNA library is derived from an organism different from the type of organism from which the labeled sequence was derived.

Alternatively, the labeled fragment may be used to screen a genomic library derived from the organism of interest, again, using appropriately stringent conditions. Low stringency conditions are well known to those of skill in the art, and will vary predictably depending on the specific organisms from which the library and the labeled sequences are derived. For guidance regarding such conditions see, for example, Sambrook, et al., 1989, Molecular Cloning, A Laboratory Manual, Second Edition, Cold Spring Harbor Press, N.Y.; and Ausubel, et al., 1989, Current Protocols in Molecular Biology, Green Publishing Associates and Wiley Interscience, N.Y.

Further, a PBC retroviral genome allelic variant may be isolated from, for example, human nucleic acid, by performing PCR using two degenerate oligonucleotide primer pools designed on the basis of nucleotide sequences disclosed herein. The template for the reaction may be cDNA obtained by reverse transcription of mRNA prepared from, for example, human or non-human cell lines or tissue known or suspected to express a retroviral genome allele (such as, for example, liver tissue from individuals having PBC).

The PCR product may be subcloned and sequenced to ensure that the amplified sequences represent the sequences of a PBC retroviral genome nucleic acid sequence. The PCR fragment may then be used to isolate a full length cDNA clone by a variety of methods. For example, the amplified fragment may be labeled and used to screen a bacteriophage cDNA library. Alternatively, the labeled fragment may be used to isolate genomic clones via the screening of a genomic library.

PCR technology and rapid amplification of cDNA ends (RACE) may also be utilized to isolate full length cDNA sequences. In particular the nucleic acids of the present invention may be used to isolate the PBC associated viral genome from patients' samples, infected biliary epithelial cells, or by screening a full representation of PBC liver cDNA libraries.

In accordance with the present invention, upon identification of retroviral genomic nucleic acid molecules, the presence of retroviral particles may be determined using routine protocols known to those skilled in the art, e.g., co-culture hepatic or lymphnoid tissue samples from PBC patients with cultured cells, intra-hepatic biliary epithelial cells, cultured biliary epithelium cells, lymphnoid cells, HepG2, HCC and RH9 lympholoastoid cell lines. Evidence for retroviral infection may be determined by RT-PCR, cell morphology, electron microcopy, and Western blot of virla extracts. RNA derived from filtered use to isolate the viral genome.

Further, accordance with the present invention, RNA may be isolated, following standard procedures, from an appropriate cellular or tissue source (i.e., one known, or suspected, to express the PBC retroviral genome, such as, for example, liver tissue samples obtained through biopsy, e.g., liver biopsy or hepatectomy specimens or post-mortem from a subject with PBC). A reverse transcription reaction may be performed on the RNA using an oligonucleotide primer specific for the most 5' end of the amplified fragment for the priming of first strand synthesis. The resulting RNA/DNA hybrid may then be "tailed" with guanines using a standard terminal transferase reaction, the hybrid may be digested with RNAase H, and second strand synthesis may then be primed with a poly-C primer. Thus, cDNA sequences upstream of the amplified fragment may easily be isolated. For a review of cloning strategies that may be used, see e.g., Sambrook et al., 1989, supra.

A cDNA of a mutant allelic variant of the PBC retroviral genome may be isolated, for example, by using PCR, a technique that is well known to those of skill in the art. In this case, the first cDNA strand may be synthesized by hybridizing an oligo-dT oligonucleotide to mRNA isolated from tissue known or suspected to be expressed in an individual putatively carrying the mutant PBC retroviral allele, and by extending the new strand with reverse transcriptase. The second strand of the cDNA is then synthesized using an oligonucleotide that hybridizes specifically to the 5' end of the normal gene. Using these two primers, the product is then amplified via PCR, cloned into a suitable vector, and subjected to DNA sequence analysis through methods well known to those of skill in the art. By comparing the DNA sequence of the mutant PBC retroviral allele to that of the normal PBC retroviral allele, the mutation(s) responsible for the loss or alteration of function of the mutant PBC retroviral gene product can be ascertained.

Alternatively, a genomic library can be constructed using DNA obtained from an individual suspected of or known to carry a mutant PBC retroviral allele, or a cDNA library can be constructed using RNA from a tissue known, or suspected, to express a mutant PBC retroviral allele. An unimpaired PBC retroviral genome or any suitable fragment thereof may then be labeled and used as a probe to identify the corresponding mutant PBC retroviral allele in such libraries. Clones containing the mutant PBC retroviral sequences may then be purified and subjected to sequence analysis according to methods well known to those of skill in the art.

Additionally, an expression library can be constructed utilizing cDNA synthesized from, for example, RNA isolated from a tissue known, or suspected, to express a mutant PBC retroviral allele in an individual suspected of or known to carry such a mutant allele. In this manner, gene products made by the putatively mutant tissue may be expressed and screened using standard antibody screening techniques in conjunction with antibodies raised against the normal PBC retroviral gene product, as described, below, in Section 5.3. (For screening techniques, see, for example, Harlow and Lane, eds., 1988, "Antibodies: A Laboratory Manual", Cold Spring Harbor Press, Cold Spring Harbor.)

The invention also includes nucleic acid molecules, preferably DNA molecules, that are the complements of the nucleotide sequences of the preceding paragraphs.

5.2 Protein Products of the PBC Retroviral Genome

PBC retroviral gene products, or peptide fragments thereof, can be prepared for a variety of uses. For example, such gene products, or peptide fragments thereof, can be used for the generation of antibodies, in diagnostic assays, or for the identification of other cellular or extracellular gene products involved in the regulation of disorders, such as PBC, Sjögren's syndrome, scleroderma, SLE, autoimmune thyroiditis and various other connective tissue disorders.

In addition, PBC retroviral genome products may include proteins that represent functionally equivalent gene products. Functionally equivalent gene products may include, for example, gene products encoded by one of the PBC retroviral nucleic acid molecules described in Section 5. 1, above. In preferred embodiments, such functionally equivalent PBC retroviral gene products are naturally occurring gene products. Such an equivalent PBC retroviral gene product may contain deletions, including internal deletions, additions, including additions yielding fusion proteins, or substitutions of amino acid residues within and/or adjacent to the amino acid sequence encoded by the PBC retroviral gene sequences described, above, in Section 5. 1, but that result in a "silent" change, in that the change produces a PBC retroviral gene product with the same activity Amino acid substitutions may be made on the basis of similarity in polarity, charge, solubility, hydrophobicity, hydrophilicity, and/or the amphipathic nature of the residues involved. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

5.3 Antibodies to PBC Retroviral Gene Products

Described herein are methods for the production of antibodies capable of specifically recognizing one or more PBC retroviral gene product epitopes or epitopes of conserved variants or peptide fragments of the PBC retroviral gene products. Further, antibodies that specifically recognize mutant forms of PBC retroviral, are encompassed by the invention.

Such antibodies may include, but are not limited to, polyclonal antibodies, monoclonal antibodies (mAbs), humanized or chimeric antibodies, single chain antibodies, Fab fragments, $F(ab')_2$ fragments, fragments produced by a Fab expression library, anti-idiotypic (anti-Id) antibodies, and epitope-binding fragments of any of the above, including the polyclonal and monoclonal antibodies. Such antibodies may be used, for example, in the detection of a PBC retroviral gene product in an biological sample and may, therefore, be utilized as part of a diagnostic or prognostic technique whereby patients may be tested for abnormal levels of PBC retroviral gene products, and/or for the presence of abnormal forms of such gene products. Such antibodies may also be utilized in conjunction with, for example, compound screening schemes, for the evaluation of the effect of test compounds on PBC retroviral gene product levels and/or activity. Additionally, such antibodies can be used in conjunction with the gene therapy techniques described below, to evaluate the normal and/or engineered PBC retroviral genome expressing cells prior to their introduction into the patient.

Anti-PBC retroviral gene product antibodies may additionally be used in pharmaceutical formulations and used in methods for the treatment and/or prevention of PBC retroviral infection and associated disorders including Sjögren's syndrome, scleroderma, SLE, autoimmune thyroiditis, various connective tissue disorders, breast cancer and lymphomas.

For the production of antibodies against a PBC retroviral gene product or a PBC retrovirus various host animals may be immunized by injection with a PBC retroviral gene product or PBC retroviral particles. Such host animals may include, but are not limited to rabbits, mice, and rats, to name but a few. Various adjuvants may be used to increase the immunological response, depending on the host species, including but not limited to Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacille Calmette-Guerin) and *Corynebacterium parvum.*

Polyclonal antibodies are heterogeneous populations of antibody molecules derived from the sera of animals immunized with an antigen, or an antigenic functional derivative thereof. For the production of polyclonal antibodies, host animals such as those described above, may be immunized by injection with PBC retroviral gene product or viral particles supplemented with adjuvants as also described above.

Monoclonal antibodies, which are homogeneous populations of antibodies to a particular antigen, may be obtained by any technique that provides for the production of antibody molecules by continuous cell lines in culture. These include, but are not limited to, the hybridoma technique of Kohler and Milstein, (1975, Nature 256:495–497; and U.S. Pat. No. 4,376,110), the human B-cell hybridoma technique (Kosbor et al., 1983, Immunology Today 4:72; Cole et al., 1983, Proc. Natl. Acad. Sci. USA 80:2026–2030), and the EBV-hybridoma technique (Cole et al., 1985, Monoclonal Antibodies And Cancer Therapy, Alan R. Liss, Inc., pp. 77–96). Such antibodies may be of any immunoglobulin class including IgG, IgM, IgE, IgA, IgD and any subclass thereof. The hybridoma producing the mAb of this invention may be cultivated in vitro or in vivo. Production of high titers of mAbs in vivo makes this the presently preferred method of production.

In addition, techniques developed for the production of "chimeric antibodies" (Morrison, et al., 1984, Proc. Natl. Acad. Sci., 81:6851–6855; Neuberger, et al., 1984, Nature 312:604–608; Takeda, et al., 1985, Nature, 314:452–454) by splicing the genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region. (See, e.g., Cabilly et al., U.S. Pat. No. 4,816,567; and Boss et al., U.S. Pat. No. 4,816,397, which are incorporated herein by reference in their entirety.)

In addition, techniques have been developed for the production of humanized antibodies. (See, e.g., Queen, U.S. Pat. No. 5,585,089, which is incorporated herein by reference in its entirety.) An immunoglobulin light or heavy chain variable region consists of a "framework" region interrupted by three hypervariable regions, referred to as complementarily determining regions (CDRs). The extent of the framework region and CDRs have been precisely defined (see, "Sequences of Proteins of Immunological Interest", Kabat, E. et al., U.S. Department of Health and Human Services (1983) ). Briefly, humanized antibodies are antibody molecules from non-human species having one or more CDRs from the non-human species and a framework region from a human immunoglobulin molecule.

Alternatively, techniques described for the production of single chain antibodies (U.S. Pat. No. 4,946,778; Bird, 1988, Science 242:423–426; Huston, et al., 1988, Proc. Natl. Acad. Sci. USA 85:5879–5883; and Ward, et al., 1989, Nature 334:544–546) can be adapted to produce single chain antibodies against PBC retroviral particles and PBC retroviral gene products. Single chain antibodies are formed by linking the heavy and light chain fragments of the Fv region via an amino acid bridge, resulting in a single chain polypeptide.

Antibody fragments that recognize specific epitopes may be generated by known techniques. For example, such fragments include but are not limited to: the F(ab')$_2$ fragments, which can be produced by pepsin digestion of the antibody molecule and the Fab fragments, which can be generated by reducing the disulfide bridges of the F(ab')$_2$ fragments. Alternatively, Fab expression libraries may be constructed (Huse, et al., 1989, Science 246:1275–1281) to allow rapid and easy identification of monoclonal Fab fragments with the desired specificity.

5.4. Uses of PBC Retroviral Gene Sequences Gene Products, and Antibodies

Described herein are various applications of isolated PBC retroviral particles, gene sequences, PBC retroviral gene products, including peptide fragments and fusion proteins thereof, and of antibodies directed against PBC retroviral gene products and peptide fragments thereof. Such applications include, for example, characterization of the complete genome of the PBC retrovirus; identification and characterization of novel retroviruses, prognostic and diagnostic evaluation of an infection by PBC retrovirus or associated disorders, including Sjögren's syndrome, scleroderma, SLE, autoimmune thyroiditis, various connective tissue disorders, breast cancer and lymphomas, and the identification of subjects with a predisposition to such disorders.

Additionally, such applications include methods for the treatment of infection by PBC retrovirus or associated disorders, including Sjögren's syndrome, scleroderma, SLE, autoimmune thyroiditis, various connective tissue disorders, breast cancer and lymphomas, as described below and for the identification of compounds that modulate the expression of the PBC retroviral gene and/or the synthesis or activity of the PBC retroviral gene product.

5.5 Diagnosis of PBC Associated Retrovirus and Related Disorders

A variety of methods can be employed for the diagnostic and prognostic evaluation of PBC retrovirus infection and related disorders PBC and for the identification of subjects having a predisposition to such disorders.

Such methods may, for example, utilize reagents such as the PBC retroviral gene nucleotide sequences described in Sections 5.1, and antibodies directed against PBC retroviral gene products, including peptide fragments thereof, as described, above, in Section 5.3. Specifically, such reagents may be used, for example, for:

(1) the detection of the presence of PBC retroviral nucleotide sequences;

(2) the detection of presence of PBC retroviral gene product.

The detection methods of the present invention can be utilized in pharmacogenetic methods to monitor and to optimize therapeutic drug treatments.

The methods described herein may be performed, for example, by utilizing pre-packaged diagnostic kits comprising at least one specific PBC retroviral nucleic acid or anti-PBC retroviral gene product antibody reagent described herein, which may be conveniently used, e.g., in clinical settings, to diagnose patients exhibiting PBC and infection by the PBC retrovirus.

In addition, methods which measure the immunoreactivity of a test sample to serum or antibodies specific for PBC-associated virus may be used for the diagnostic and prognostic evaluation of PBC retrovirus infection and related disorders PBC and for the identification of subjects having a predisposition to such disorders.

5.6 Detection of PBC Retroviral Nucleic Acid Molecules

A variety of methods can be employed to screen for the presence of PBC retroviral to detect and/or assay levels of PBC retroviral nucleic acid sequences.

PBC retroviral nucleic acid sequences may be used in hybridization or amplification assays of biological samples to detect levels and abnormalities involving PBC retroviral genome structure, including point mutations, insertions, deletions, inversions, translocations and chromosomal rearrangements. Such assays may include, but are not limited to, Southern analyses, single-stranded conformational polymorphism analyses (SSCP), and PCR analyses.

Diagnostic methods for the detection of PBC retroviral gene-specific mutations can involve for example, contacting and incubating nucleic acids obtained from a sample, e.g., derived from a patient sample or other appropriate cellular source with one or more labeled nucleic acid reagents including recombinant DNA molecules, cloned genes or degenerate variants thereof, such described in Section 5.1, above, under conditions favorable for the specific annealing of these reagents to their complementary sequences within or flanking the PBC retroviral genome. The diagnostic methods of the present invention further encompass contacting and incubating nucleic acids for the detection of single nucleotide mutations or polymorphisms of the PBC retroviral genome.

After incubation, all non-annealed nucleic acids are removed from the nucleic acid: PBC retroviral molecule hybrid. The presence of nucleic acids that have hybridized, if any such molecules exist, is then detected. Using such a detection scheme, the nucleic acid from the cell type or tissue of interest can be immobilized, for example, to a solid support such as a membrane, or a plastic surface such as that on a microtiter plate or polystyrene beads. In this case, after incubation, non-annealed, labeled nucleic acid reagents of the type described in Section 5.1 are easily removed. Detection of the remaining, annealed, labeled PBC retroviral nucleic acid reagents is accomplished using standard techniques well-known to those in the art. The PBC retroviral gene sequences to which the nucleic acid reagents have annealed can be compared to the annealing pattern expected from a normal PBC retroviral gene sequence in order to determine whether a PBC retroviral gene mutation is present.

In a preferred embodiment, PBC retroviral mutations or polymorphisms can be detected by using a microassay of PBC retroviral nucleic acid sequences immobilized to a substrate or "gene chip" (see, e.g. Cronin, et al., 1996, Human Mutation 7:244–255).

Alternative diagnostic methods for the detection of PBC retroviral gene specific nucleic acid molecules, in patient samples or other appropriate cell sources, may involve their amplification, e.g., by PCR (the experimental embodiment set forth in Mullis, 1987, U.S. Pat. No. 4,683,202), followed by the analysis of the amplified molecules using techniques well known to those of skill in the art, such as, for example, those listed above.

Those PBC retroviral nucleic acid sequences which are preferred for such amplification-related diagnostic screening analyses are oligonucleotide primers which are described in the Working Examples herein.

Additional PBC retroviral nucleic acid sequences which are preferred for such amplification-related analyses are those which will detect the presence of an PBC retroviral polymorphism. Such polymorphisms include ones which represent mutations associated with an PBC retroviral-mediated disorders.

Additionally, well-known genotyping techniques can be performed to identify individuals carrying PBC retroviral gene mutations. Such techniques include, for example, the use of restriction fragment length polymorphisms (RFLPs), which involve sequence variations in one of the recognition sites for the specific restriction enzyme used.

Further, improved methods for analyzing DNA polymorphisms, which can be utilized for the identification of PBC retroviral gene-specific mutations, have been described that capitalize on the presence of variable numbers of short, tandemly repeated DNA sequences between the restriction enzyme sites. For example, Weber (U.S. Pat. No. 5,075,217) describes a DNA marker based on length polymorphisms in blocks of (dC-dA)n-(dG-dT)n short tandem repeats. The average separation of (dC-dA)n-(dG-dT)n blocks is estimated to be 30,000–60,000 bp. Markers that are so closely spaced exhibit a high frequency co-inheritance, and are extremely useful in the identification of genetic mutations, such as, for example, mutations within the PBC retroviral gene, and the diagnosis of diseases and disorders related to PBC retroviral mutations.

Also, Caskey et al. (U.S. Pat. No. 5,364,759) describe a DNA profiling assay for detecting short tri and tetra nucleotide repeat sequences. The process includes extracting the DNA of interest, such as the PBC retroviral gene, amplifying the extracted DNA, and labelling the repeat sequences to form a genotypic map of the individual's DNA.

Other methods well known in the art may be used to identify single nucleotide polymorphisms (SNPs), including biallelic SNPs or biallelic markers which have two alleles, both of which are present at a fairly high frequency in a population. Conventional techniques for detecting SNPs include, e.g., conventional dot blot analysis, single stranded conformational polymorphism (SSCP) analysis (see, e.g., Orita et al., 1989, Proc. Natl. Acad. Sci. USA 86:2766–2770), denaturing gradient gel electrophoresis (DGGE), heterodulex analysis, mismatch cleavage detection, and other routine techniques well known in the art (see, e.g., Sheffield et al., 1989, Proc. Natl. Acad. Sci. 86:5855–5892; Grompe, 1993, Nature Genetics 5:111–117). Alternative, preferred methods of detecting and mapping SNPs involve microsequencing techniques wherein an SNP site in a target DNA is detecting by a single nucleotide primer extension reaction (see, e.g., Goelet et al., PCT Publication No. WO92/15712; Mundy, U.S. Pat. No. 4,656,127; Vary and Diamond, U.S. Pat. No. 4,851,331; Cohen et al., PCT Publication No. WO91/02087; Chee et al., PCT Publication No. WO95/11995; Landegren et al., 1988, *Science* 241:1077–1080; Nicerson et al., 1990, *Proc. Natl. Acad. Sci. U.S.A.* 87:8923–8927; Pastinen et al.,1997, *Genome Res.* 7:606–614; Pastinen et al., 1996, *Clin. Chem.* 42:1391–1397; Jalanko et al., 1992, *Clin. Chem.* 38:39–43; Shumaker et al., 1996, *Hum. Mutation* 7:346–354; Caskey et al., PCT Publication No. WO 95/00669).

The level of PBC retroviral gene expression can also be assayed. For example, RNA from a cell type or tissue known, or suspected, to express the PBC retroviral gene, such as bile duct or liver tissue, may be isolated and tested utilizing hybridization or PCR techniques such as are described, above. The isolated cells can be derived from cell culture or from a patient. The analysis of cells taken from culture may be a necessary step in the assessment of cells to be used as part of a cell-based gene therapy technique or, alternatively, to test the effect of compounds on the expression of the PBC retroviral gene. Such analyses may reveal both quantitative and qualitative aspects of the expression pattern of the PBC retroviral gene, including activation or inactivation of PBC retroviral gene expression.

In one embodiment of such a detection scheme, a cDNA molecule is synthesized from an RNA molecule of interest (e.g., by reverse transcription of the RNA molecule into cDNA). A sequence within the cDNA is then used as the template for a nucleic acid amplification reaction, such as a PCR amplification reaction, or the like. The nucleic acid reagents used as synthesis initiation reagents (e.g., primers) in the reverse transcription and nucleic acid amplification steps of this method are chosen from among the PBC retroviral gene nucleic acid reagents described in Section 5.1. The preferred lengths of such nucleic acid reagents are at least 9–30 nucleotides. For detection of the amplified product, the nucleic acid amplification may be performed using radioactively or non-radioactively labeled nucleotides. Alternatively, enough amplified product may be made such that the product may be visualized by standard ethidium bromide staining or by utilizing any other suitable nucleic acid staining method.

Additionally, it is possible to perform such PBC retroviral gene expression assays "in situ", i.e., directly upon tissue sections (fixed and/or frozen) of patient tissue obtained from biopsies. or resections, such that no nucleic acid purification is necessary. Nucleic acid reagents such as those described in Section 5.1 may be used as probes and/or primers for such in situ procedures (see, for example, Nuovo, G. J., 1992, "PCR In Situ Hybridization: Protocols And Applications", Raven Press, NY).

Alternatively, if a sufficient quantity of the appropriate cells can be obtained, standard Northern analysis can be performed to determine the level of mRNA expression of the PBC retroviral gene.

5.7 Inhibitory Antisense, Ribozyme and Triple Helix Approaches

In another embodiment, symptoms of PBC retroviral-mediated disorders may be ameliorated by decreasing the level of PBC retroviral gene expression and/or PBC retroviral gene product activity by using PBC retroviral gene sequences in conjunction with well-known antisense, gene "knock-out," ribozyme and/or triple helix methods to decrease the level of PBC retroviral gene expression. Among the compounds that may exhibit the ability to modulate the activity, expression or synthesis of the PBC retroviral gene, including the ability to ameliorate the symptoms of a PBC retroviral-mediated disorder, are antisense, ribozyme, and triple helix molecules. Such molecules may be designed to reduce or inhibit either unimpaired, or if appropriate, mutant target gene activity. Techniques for the production and use of such molecules are well known to those of skill in the art.

Antisense RNA and DNA molecules act to directly block the translation of mRNA by hybridizing to targeted mRNA and preventing protein translation. Antisense approaches involve the design of oligonucleotides that are complementary to a target gene mRNA. The antisense oligonucleotides will bind to the complementary target gene mRNA transcripts and prevent translation. Absolute complementarily, although preferred, is not required.

A sequence "complementary" to a portion of an RNA, as referred to herein, means a sequence having sufficient complementarily to be able to hybridize with the RNA, forming a stable duplex; in the case of double-stranded antisense nucleic acids, a single strand of the duplex DNA may thus be tested, or triplex formation may be assayed. The ability to hybridize will depend on both the degree of complementarily and the length of the antisense nucleic acid. Generally, the longer the hybridizing nucleic acid, the more base mismatches with an RNA it may contain and still formn a stable duplex (or triplex, as the case may be). One skilled in the art can ascertain a tolerable degree of mismatch by use of standard procedures to determine the melting point of the hybridized complex.

In one embodiment, oligonucleotides complementary to non-coding regions of the PBC retroviral gene could be used in an antisense approach to inhibit translation of endogenous PBC retroviral mRNA. Antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

Regardless of the choice of target sequence, it is preferred that in vitro studies are first performed to quantitate the ability of the antisense oligonucleotide to inhibit gene expression. It is preferred that these studies utilize controls that distinguish between antisense gene inhibition and non-specific biological effects of oligonucleotides. It is also preferred that these studies compare levels of the target RNA or protein with that of an internal control RNA or protein. Additionally, it is envisioned that results obtained using the antisense oligonucleotide are compared with those obtained using a control oligonucleotide. It is preferred that the control oligonucleotide is of approximately the same length as the test oligonucleotide and that the nucleotide sequence of the oligonucleotide differs from the antisense sequence no more than is necessary to prevent specific hybridization to the target sequence.

The oligonucleotides can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger, et al., 1989, Proc. Natl. Acad. Sci. U.S.A. 86:6553–6556; Lemaitre, et al., 1987, Proc. Natl. Acad. Sci. U.S.A. 84:648–652; PCT Publication No. WO88/09810, published Dec. 15, 1988) or the blood-brain barrier (see, e.g., PCT Publication No. WO89/10134, published Apr. 25, 1988), hybridization-triggered cleavage agents (see, e.g., Krol et al., 1988, BioTechniques 6:958–976) or intercalating agents (see, e.g., Zon, 1988, Pharm. Res. 5:539–549). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including but not limited to 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3) w, and 2,6-diaminopurine.

The antisense oligonucleotide may also comprise at least one modified sugar moiety selected from the group including but not limited to arabinose, 2-fluoroarabinose, xylulose, and hexose.

In yet another embodiment, the antisense oligonucleotide comprises at least one modified phosphate backbone selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an α-anomeric oligonucleotide. An α-anomeric oligonucleotide forms specific double-stranded hybrids with complementary RNA in which, contrary to the usual β-units, the strands run parallel to each other (Gautier, et al., 1987, Nucl. Acids Res. 15:6625–6641). The oligonucleotide is a 2'-0-methylribonucleotide (Inoue, et al., 1987, Nucl. Acids Res. 15:6131–6148), or a chimeric RNA-DNA analogue (Inoue, et al., 1987, FEBS Lett. 215:327–330).

Oligonucleotides of the invention may be synthesized by standard methods known in the art, e.g., by use of an automated DNA synthesizer (such as are commercially available from Biosearch, Applied Biosystems, etc.). As examples, phosphorothioate oligonucleotides may be synthesized by the method of Stein, et al. (1988, Nucl. Acids Res. 16:3209), methylphosphonate oligonucleotides can be prepared by use of controlled pore glass polymer supports (Sarin, et al., 1988, Proc. Natl. Acad. Sci. U.S.A. 85:7448–7451), etc.

While antisense nucleotides complementary to the target gene coding region sequence could be used, those complementary to the transcribed, untranslated region are most preferred.

Antisense molecules should be delivered to cells that express the target gene in vivo. A number of methods have been developed for delivering antisense DNA or RNA to cells; e.g., antisense molecules can be injected directly into the tissue site, or modified antisense molecules, designed to target the desired cells (e.g., antisense linked to peptides or antibodies that specifically bind receptors or antigens expressed on the target cell surface) can be administered systemically.

However, it is often difficult to achieve intracellular concentrations of the antisense sufficient to suppress translation of endogenous mRNAs. Therefore a preferred approach utilizes a recombinant DNA construct in which the antisense oligonucleotide is placed under the control of a strong pol III or pol II promoter. The use of such a construct to transfect target cells in the patient will result in the transcription of sufficient amounts of single stranded RNAs that will form complementary base pairs with the endogenous target gene transcripts and thereby prevent translation of the target gene mRNA. For example, a vector can be introduced e.g., such that it is taken up by a cell and directs the transcription of an antisense RNA. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others known in the art, used for replication and expression in mammalian cells. Expression of the sequence encoding the antisense RNA can be by any promoter known in the art to act in mammalian, preferably human cells. Such promoters can be inducible or constitutive. Such promoters include but are not limited to: the SV40 early promoter region (Bemoist and Chambon, 1981, Nature 290:304–310), the promoter contained in the 3' long terminal repeat of Rous sarcoma virus (Yamamoto, et al., 1980, Cell 22:787–797), the herpes thymidine kinase promoter (Wagner, et al., 1981, Proc. Natl. Acad. Sci. U.S.A. 78:1441–1445), the regulatory sequences of the metallothionein gene (Brinster, et al., 1982, Nature 296:39–42), etc. Any type of plasmid, cosmid, YAC or viral vector can be used to prepare the recombinant DNA construct which can be introduced directly into the tissue site. Alternatively, viral vectors can be used that selectively infect the desired tissue, in which case administration may be accomplished by another route (e.g., systemically).

Ribozyme molecules designed to catalytically cleave target gene mRNA transcripts can also be used to prevent translation of target gene mRNA and, therefore, expression of target gene product. (See, e.g., PCT International Publication WO90/11364, published Oct. 4, 1990; Sarver, et al., 1990, Science 247, 1222–1225).

Ribozymes are enzymatic RNA molecules capable of catalyzing the specific cleavage of RNA. (For a review, see Rossi, 1994, Current Biology 4:469–471). The mechanism of ribozyme action involves sequence specific hybridization of the ribozyme molecule to complementary target RNA, followed by an endonucleolytic cleavage event. The composition of ribozyme molecules must include one or more sequences complementary to the target gene mRNA, and must include the well known catalytic sequence responsible for mRNA cleavage. For this sequence, see, e.g., U.S. Pat. No. 5,093,246, which is incorporated herein by reference in its entirety.

While ribozymes that cleave mRNA at site specific recognition sequences can be used to destroy target gene mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Myers, 1995, *Molecular Biology and Biotechnology: A Comprehensive Desk Reference,* VCH Publishers, New York, (see especially FIG. 4, page 833) and in Haseloff and Gerlach, 1988, Nature, 334:585–591, which is incorporated herein by reference in its entirety.

Preferably the ribozyme is engineered so that the cleavage recognition site is located near the 5' end of the target gene mRNA, i.e., to increase efficiency and minimize the intracellular accumulation of non-functional mRNA transcripts.

The ribozymes of the present invention also include RNA endoribonucleases (hereinafter "Cech-type ribozymes") such as the one that occurs naturally in *Tetrahymena thermophila* (known as the IVS, or L-19 IVS RNA) and that has been extensively described by Thomas Cech and collaborators (Zaug, et al., 1984, Science, 224:574–578; Zaug and Cech, 1986, Science, 231:470–475; Zaug, et al., 1986, Nature, 324:429–433; published International patent application No. WO 88/04300 by University Patents Inc.; Been and Cech, 1986, Cell, 47:207–216). The Cech-type ribozymes have an eight base pair active site which hybridizes to a target RNA sequence whereafter cleavage of the target RNA takes place. The invention encompasses those Cech-type ribozymes which target eight base-pair active site sequences that are present in the target gene.

As in the antisense approach, the ribozymes can be composed of modified oligonucleotides (e.g., for improved stability, targeting, etc.) and should be delivered to cells that express the target gene in vivo. A preferred method of delivery involves using a DNA construct "encoding" the ribozyme under the control of a strong constitutive pol III or pol II promoter, so that transfected cells will produce sufficient quantities of the ribozyme to destroy endogenous target gene messages and inhibit translation. Because ribozymnes unlike antisense molecules, are catalytic, a lower intracellular concentration is required for efficiency.

Endogenous target gene expression can also be reduced by inactivating or "knocking out" the target gene or its promoter using targeted homologous recombination (e.g., see Smithies, et al., 1985, Nature 317:230–234; Thomas and Capecchi, 1987, Cell 51:503–512; Thompson, et al., 1989, Cell 5:313–321; each of which is incorporated by reference herein in its entirety). For example, a mutant, non-functional target gene (or a completely unrelated DNA sequence) flanked by DNA homologous to the endogenous target gene (either the coding regions or regulatory regions of the target gene) can be used, with or without a selectable marker and/or a negative selectable marker, to transfect cells that express the target gene in vivo. Insertion of the DNA construct, via targeted homologous recombination, results in inactivation of the target gene. Such approaches are particularly suited in the agricultural field where modifications to ES (embryonic stem) cells can be used to generate animal offspring with an inactive target gene (e.g., see Thomas and Capecchi, 1987 and Thompson, 1989, supra). However this approach can be adapted for use in humans provided the recombinant DNA constructs are directly administered or targeted to the required site in vivo using appropriate viral vectors.

Alternatively, endogenous target gene expression can be reduced by targeting deoxyribonucleotide sequences complementary to the regulatory region of the target gene (i.e., the target gene promoter and/or enhancers) to form triple helical structures that prevent transcription of the target gene in target cells in the body. (See generally, Helene, 1991, Anticancer Drug Des., 6(6):569–584; Helene, et al., 1992, Ann. N.Y. Acad. Sci., 660:27–36; and Maher, 1992, Bioassays 14(12):807–815).

Nucleic acid molecules to be used in triplex helix formation for the inhibition of transcription should be single stranded and composed of deoxynucleotides. The base composition of these oligonucleotides must be designed to promote triple helix formation via Hoogsteen base pairing rules, which generally require sizeable stretches of either purines or pyrimidines to be present on one strand of a duplex. Nucleotide sequences may be pyrimidine-based, which will result in TAT and CGC$^+$ triplets across the three associated strands of the resulting triple helix. The pyrimidine-rich molecules provide base complementarily to a purine-rich region of a single strand of the duplex in a parallel orientation to that strand. In addition, nucleic acid molecules may be chosen that are purine-rich, for example, contain a stretch of G residues. These molecules will form a triple helix with a DNA duplex that is rich in GC pairs, in which the majority of the purine residues are located on a single strand of the targeted duplex, resulting in GGC triplets across the three strands in the triplex.

Alternatively, the potential sequences that can be targeted for triple helix formation may be increased by creating a so called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

In instances wherein the antisense, ribozyme, and/or triple helix molecules described herein are utilized to inhibit mutant gene expression, it is possible that the technique may so efficiently reduce or inhibit the transcription (triple helix) and/or translation (antisense, ribozyme) of mRNA produced by normal target gene alleles that the possibility may arise wherein the concentration of normal target gene product present may be lower than is necessary for a normal phenotype. In such cases, to ensure that substantially normal levels of target gene activity are maintained, therefore, nucleic acid molecules that encode and express target gene polypeptides exhibiting normal target gene activity may, be introduced into cells via gene therapy methods such as those described, below, in Section 5.9.2 that do not contain sequences susceptible to whatever antisense, ribozyme, or triple helix treatments are being utilized. Alternatively, in instances whereby the target gene encodes an extracellular protein, it may be preferable to co-administer normal target gene protein in order to maintain the requisite level of target gene activity.

Anti-sense RNA and DNA, ribozyme, and triple helix molecules of the invention may be prepared by any method known in the art for the synthesis of DNA and RNA molecules, as discussed above. These include techniques for chemically synthesizing oligodeoxyribonucleotides and oligoribonucleotides well known in the art such as for example solid phase phosphoramidite chemical synthesis. Alternatively, RNA molecules may be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

5.8 Pharmaceutical Preparations and Methods of Administration

The present invention relates to methods of treating individuals infected with PBC retrovirus. In particular, the present invention relates to combinations of antiviral and immunomodulation therapy to control viral replication and disease symptoms in individuals infected with PBC retrovirus. The present invention relates to methods of treating or inhibiting PBC retroviral infection with antiviral agents, such as cytokines, inhibitors of reverse transcriptase, inhibitors of viral capping, and inhibitors of viral protease. The present invention further relates to vaccines and other prophylectic treatments to prevent disease in genetically susceptible individuals.

As provided herein, antiviral agents have been demonstrated to reduce or inhibit PBC viral load and/or infection in patients infected with PBC as determined by histological analysis. In accordance with the present invention antiviral agents which may be used to reduce PBC viral cord and/or infection include, but are not limited to, reverse transcriptase inhibitors, viral protease inhibitors, glycosylation inhibitors; those which act on a different target molecule involved in viral transmission; those which act on a different loci of the same molecule; and those which prevent or reduce the occurrence of viral resistance. One skilled in the art would know of a wide variety of antiviral therapies which exhibit the above modes of activity including: Nucleoside derivatives are modified forms of purine and pyrimidine nucleosides which are the building blocks of RNA and DNA which include but are not limited to, 2',3'-dideoxyadenosine (ddA); 2',3'-dideoxyguanosine (ddG); 2',3'-dideoxyinosine (ddI); 2',3'-dideoxycytidine (ddC); 2',3'-dideoxythymidine (ddT); 2',3'-dideoxy-dideoxythymidine (d4T) and 3'-azido-2',3'-dideoxythymidine (AZT). Alternatively, halogenated nucleoside derivatives may be used, preferably 2',3'-dideoxy-2'-fluoronucleosides including, but not limited to, 2',3'-dideoxy-2'-fluoroadenosine; 2',3'-dideoxy-2'-fluoroinosine; 2',3'-dideoxy-2'-fluorothymidine; 2',3'-dideoxy-2'-fluorocytosine; and 2',3'-dideoxy-2',3'-didehydro-2'-fluoronucleosides including, but not limited to 2',3'-dideoxy-2',3'-didehydro-2'-fluorothymidine (Fd4T). Preferably, the 2',3'-dideoxy-2'-fluoronucleosides of the invention are those in which the fluorine linkage is in the beta configuration, including, but not limited to, 2'3'-dideoxy-2'-beta-fluoroadenosine (F-ddA), 2',3'-dideoxy-2'-beta-fluoroinosine (F-ddI), and 2',3'-dideoxy-2'-beta-fluorocytosine (F-ddC).

Viral protease inhibitors, including but not limited to, Invirase (saquinavir, Roche), ABT-538 (Abbott, CAS Reg. No. 155213-67-5), AG1343 (Burroughs Wellcome/Glaxo, CAS Reg. No. 161814-49-9). Protease inhibitors are generally thought to work primarily during or after assembly (i.e., viral budding) to inhibit maturation of virions to a mature infectious state. For example, ABT-538 has been shown to have potent antiviral activity in vitro and favorable pharmokinetic and safety profiles in vivo (Ho, et al., 1995, Nature 373: 123–126).

The compounds that are determined to affect PBC retroviral gene expression or gene product activity can be administered to a patient at therapeutically effective doses to treat or ameliorate a PBC retroviral-mediated disorder. A therapeutically effective dose refers to that amount of the compound sufficient to result in amelioration of symptoms of such a disorder.

5.8.1 Effective Dose

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. As described herein, the present invention also encompasses a cell culture model for PBC, including co-cultures of hepatic tissue infected with PBC and immortalized cell lines, which may be used to establish $LD_{50}/ED_{50}$ ratios of compounds to be used in the treatment of PBC. Compounds that exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

5.8.2 Formulations and Use

Pharmaceutical compositions for use in accordance with the present invention may be formulated in conventional manner using one or more physiologically acceptable carriers or excipients.

Thus, the compounds and their physiologically acceptable salts and solvates may be formulated for administration by inhalation or insufflation (either through the mouth or the nose) or oral, buccal, parenteral or rectal administration.

For oral administration, the pharmaceutical compositions may take the form of, for example, tablets or capsules prepared by conventional means with pharmaceutically acceptable excipients such as binding agents (e.g., pregelatinised maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and preservatives (e.g., methyl or propyl-p-hydroxybenzoates or sorbic acid). The preparations may also contain buffer salts, flavoring, coloring and sweetening agents as appropriate.

Preparations for oral administration may be suitably formulated to give controlled release of the active compound.

For buccal administration the compositions may take the form of tablets or lozenges formulated in conventional manner.

For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for administration.

5.9 Vaccine Formulations and Methods of Administration

The PBC associated virus in an attenuated form and PBC associated virus gene products have use in vaccine preparations and in immunoassays, e.g., to detect or measure in a sample of body fluid from a vaccinated subject the presence of antibodies to the antigen, and thus to diagnose infection and/or to monitor immune response of the subject subsequent to vaccination.

The preparation of vaccines containing an immunogenic polypeptide as the active ingredient is known to one skilled in the art.

5.9.1 Determination of Vaccine Efficacy

The immunopotency of the PBC associated virus in an attenuated form and PBC associated virus gene products can be determined by monitoring the immune response in test animals following immunization with the antigen, or by use of any immunoassay known in the art. Generation of a humoral (antibody) response and/or cell-mediated immunity, may be taken as an indication of an immune response. Test animals may include mice, hamsters, dogs, cats, monkeys, rabbits, chimpanzees, etc., and eventually human subjects.

Methods of introducing the vaccine may include oral, intracerebral, intradermal, intramuscular, intraperitoneal, intravenous, subcutaneous, intranasal or any other standard routes of immunization. The immune response of the test subjects can be analyzed by various approaches such as: the reactivity of the resultant immune serum to the antigen, as assayed by known techniques, e.g., immunosorbant assay (ELISA), immunoblots, radioimmunoprecipitations, etc., or in the case where the antigen displays antigenicity or immunogenicity, by protection of the immunized host from infection by the PBC associated retrovinus and/or attenuation of symptoms due to infection in the immunized host.

As one example of suitable animal testing of a vaccine, the vaccine of the invention may be tested in rabbits for the ability to induce an antibody response to the antigen. Male specific-pathogen-free (SPF) young adult New Zealand White rabbits may be used. The test group each receives a fixed concentration of the vaccine. A control group receives an injection of 1 mM Tris-HCl pH 9.0 without the antigen.

Blood samples may be drawn from the rabbits every one or two weeks, and serum analyzed for antibodies to the viral protein. The presence of antibodies specific for the antigen may be assayed, e.g., using an ELISA.

5.9.2 Vaccine Formulations

Suitable preparations of such vaccines include injectables, either as liquid solutions or suspensions; solid forms suitable for solution in, suspension in, liquid prior to injection, may also be prepared. The preparation may also be emulsified, or the polypeptides encapsulated in liposomes. the active immunogenic ingredients are often mixed with excipients which are pharmaceutically acceptable and compatible with the active ingredient. Suitable excipients are, for example, water saline, dextrose, glycerol, ethanol, or the like and combinations thereof. In addition, if desired, the vaccine preparation may also include minor amounts of auxiliary substances such as wetting or emulsifying agents, pH buffering agents, and/or adjuvants which enhance the effectiveness of the vaccine.

In one embodiment of the invention, recombinant vaccines may be formulated which express the PBC retroviral nucleic acid molecules of the present invention. In yet another embodiment, vaccines may be formulated which comprise the isolated PBC associated vetrovirus which has been formulated using conventional techniques to “kill” or attenuate the virus. Such techniques include heat inactivation, or treatment with formalin, formaldehyde or β-propiolactone.

Examples of adjuvants which maybe effective, include, but are not limited to: aluminum hydroxide, N-acetyl-muramyl-L-threonyl-D-isoglutamine (thr-MDP), N-acetyl-nor-muramyl-L-alanyl-D-isoglutamine, N-acetylmuramyl-L-alanyl-D-isoglutaminyl-L-alanine-2-(1'-2'-dipalmitoyl-sn-glycero-3-hydroxyphosphoryloxy)-ethylamine.

The effectiveness of an adjuvant may be determined by measuring the induction of antibodies directed against an immunogenic polypeptide containing a viral polypeptide epitope, the antibodies resulting from administration of this polypeptide in vaccines which are also comprised of the various adjuvants.

The polypeptides may be formulated into the vaccine as neutral or salt forms. Pharmaceutically acceptable salts include the acid addition salts (formed with free amino groups of the peptide) and which are formed with inorganic acids, such as, for example, hydrochloric or phosphoric acids, or organic acids such as acetic, oxalic, tartaric, maleic, and the like. Salts formed with free carboxyl groups may also be derived from inorganic bases, such as, for example, sodium potassium, ammonium, calcium, or ferric hydroxides, and such organic bases as isopropylamine, trimethylamine, 2-ethylamino ethanol, histidine, procaine and the like.

The vaccines of the invention may be multivalent or univalent. Multivalent vaccines are made from recombinant viruses that direct the expression of more than one antigen.

Many methods may be used to introduce the vaccine formulations of the invention; these include but are not limited to oral, intradermal, intramuscular, intraperitoneal, intravenous, subcutaneous, intranasal routes, and via scarification (scratching through the top layers of skin, e.g., using a bifurcated needle).

The patient to which the vaccine is administered is preferably a mammal, most preferably a human, but can also be a non-human animal including but not limited to cows, horses, sheep, pigs, fowl (e.g., chickens), goats, cats, dogs, hamsters, mice and rats.

The vaccine formulations of the invention comprise an effective immunizing amount of the viral protein and a pharmaceutically acceptable carrier or excipient. Vaccine preparations comprise an effective immunizing amount of one or more antigens and a pharmaceutically acceptable carrier or excipient. Pharmaceutically acceptable carriers are well known in the art and include but are not limited to saline, buffered saline, dextrose, water, glycerol, sterile isotonic aqueous buffer, and combinations thereof. One example of such an acceptable carrier is a physiologically balanced culture medium containing one or more stabilizing agents such as stabilized, hydrolyzed proteins, lactose, etc. The carrier is preferably sterile. The formulation should suit the mode of administration.

The composition, if desired, can also contain minor amounts of wetting or emulsifying agents, or pH buffering agents. The composition can be a liquid solution, suspension, emulsion, tablet, pill, capsule, sustained release formulation, or powder. Oral formulation can include standard carriers such as pharmaceutical grades of mannitol, lactose, starch, magnesium stearate, sodium saccharine, cellulose, magnesium carbonate, etc.

Generally, the ingredients are supplied either separately or mixed together in unit dosage form, for example, as a dry lyophilized powder or water free concentrate in a hermetically sealed container such as an ampoule or sachette indicating the quantity of active agent. Where the composition is administered by injection, an ampoule of sterile diluent can be provided so that the ingredients may be mixed prior to administration.

The precise dose of vaccine preparation to be employed in the formulation will also depend on the route of administration, and the nature of the patient, and should be decided according to the judgment of the practitioner and each patient's circumstances according to standard clinical techniques. An effective immunizing amount is that amount sufficient to produce an immune response to the antigen in the host to which the vaccine preparation is administered.

Use of purified antigens as vaccine preparations can be carried out by standard methods. For example, the purified protein(s) should be adjusted to an appropriate concentration, formulated with any suitable vaccine adjuvant and packaged for use. Suitable adjuvants may include, but are not limited to: mineral gels, e.g., aluminum hydroxide; surface active substances such as lysolecithin, pluronic polyols; polyanions; peptides; oil emulsions; alum, and MDP. The immunogen may also be incorporated into liposomes, or conjugated to polysaccharides and/or other polymers for use in a vaccine formulation. In instances where the recombinant antigen is a hapten, i.e., a molecule that is antigenic in that it can react selectively with cognate antibodies, but not immunogenic in that it cannot elicit an immune response, the hapten may be covalently bound to a carrier or immunogenic molecule; for instance, a large protein such as serum albumin will confer immunogenicity to the hapten coupled to it. The hapten-carrier may be formulated for use as a vaccine.

Effective doses (immunizing amounts) of the vaccines of the invention may also be extrapolated from dose-response curves derived from animal model test systems.

The invention also provides a pharmaceutical pack or kit comprising one or more containers comprising one or more of the ingredients of the vaccine formulations of the invention. Associated with such container(s) can be a notice in the form prescribed by a governmental agency regulating the manufacture, use or sale of pharmaceuticals or biological products, which notice reflects approval by the agency of manufacture, use or sale for human administration.

The present invention thus provides a method of immunizing an animal, or treating or preventing various diseases or disorders in an animal, comprising administering to the animal an effective immunizing dose of a vaccine of the present invention.

6. EXAMPLES

The following examples describes the isolation and characterization of novel PBC retroviral nucelotides.

6.1 Electron Microscopy of PBC Biliary Epithelium and Co-culture Studies

Electron microscopy (EM) studies have been performed on biliary epithelial cells (BEC) extracted from liver transplant recipients, as well as BEC and supernatant from the lymph node co-culture studies. The particles seen in the different studies were similar in size and shape and consistent with B and D type retroviral morphology. Even though an intracisternal A-type particle was observed in one BEC during the co-culture studies, this may represent an immature form of a budding retrovirus.

In the initial EM studies of freshly isolated BEC from liver transplant recipients, sections of approximately 200 to 400 cells per patient were studied in a blinded fashion. Three of five PBC patients had evidence of several viral-like particles per cell as compared to a single virus-like particle detected in 1 of 4 patients in the comparison group. Each was approximately 100–120 nM in size and had a definable envelope as well as a dense oval nucleus consistent with a B and D type retrovirus morphology. Like HRV 5 derived from a patient with Sjögren's syndrome, the PBC virus seems to be of extremely low abundance and was only observed in 1 in 100–300 BEC. Both intra and extracellular particles were observed.

The EM studies were performed on BEC incubated after one week in the co-culture studies and assessed in a blinded fashion. One experiment with the PBC lymph node homogenate revealed an A-type particle measuring approximately 80 to 90 nm in diameter within a vesicle. The supernatant were also derived from the co-culture studies after one week, processed in the ultracentrifuge, negatively stained, and assessed in a blinded fashion. Virus-like particles were rarely encountered and found only in the PBC co-cultured supernatants. They were spherical in shape and in one particle where the negative stain had breached the viral envelope, the nucleus was central and oval consistent with a B-type retrovirus morphology.

These studies provide solid evidence that AMA reactivity can be induced in specific fashion in normal biliary epithelium by PBC lymph node homogenates. Moreover, the transmissible agent associated with the transformation of normal BEC to the phenotypic manifestation of PBC has the genomic, morphologic, and hydrodynamic properties of an exogenous B and D type retrovirus.

6.2 Retroviral Cloning Studies

Retroviral sequences derived by representational difference analysis

Representative differential analysis (RDA) was first used to determine whether an infectious agent was etiologically involved in the pathogenesis of PBC. The technique has the power to identify small amounts of microbial DNA in the "tester" material, in this case a liver sample, not present in the "driver" DNA (Lisitsyn, et al., 1993. Science. 259:946–951). This subtraction hybridization and PCR amplification methodology also has the power to detect somatic mutations, as well as genomic deletions and insertions (Lisitsyn, et al., 1993. Science. 259:946–951). In these studies, extracted DNA from the liver and skin of a PBC patient and a control patient with primary sclerosing cholangitis (PSC), were used as a tester and driver, respectively using the RDA protocol described by Lisitsyn and colleagues (Lisitsyn, et al., 1993. Science. 259:946–951). All the RDA products were cloned, sequenced and then assessed by blast searches of the NCBI databases. A proportion of the PBC RDA products were found to have the highest score homology with retroviral-like sequences, such as the immature form of a B and D type retrovirus. One product had 91% nucleotide homology with the endogenous retrovirus ERV-9, while 3 other products had either partial nucleotide or protein sequence homology with HTLV-1 envelope gene, and feline immunodeficiency virus env protein and ground squirrel hepadnaviral pol protein, respectively. In contrast, no viral or retroviral-like sequences were identified in the PSC RDA products. The following are the sequences of the RDA products identified. The following sequences may be particularly useful as genetic markers to screen a patient's serum or tissue sample for the presence of a retroviral infection S139:
GATCCTGTCCGTGATGCCAATTGTCAG-GTTCTAACAGGTCTGAGGGGAGTCGGNT-GAGCAAGTGGCGAGTGGCTGGAAAAAC GCTG-GAGGAATCGCAGACAGTTTCAATATGGCNTTAC TCACTATCTGGGTGTGAGTGAGACT GGGCAT-CAGNCATATGTACAGCTTTASNAGGN-TAACTATATGNTTTATAGATAATAGT-NGCTTGAGCCAAGCACGAGCTCATGTGTGATC (SEQ ID NO:16)

S59:
GATCGTAGTTGGCAAAAGCCTGTGATTC-CAAGGAACCTCCACAACTGTTTTAAT-GTCTTAGGTCGAGGATAAGCCGGTATAG-GTTGTATTCATTCTCGCTAAGAGCCCTGGTCCCT CTGGCTAAGATTAGGCCTAGATATTT GACCTGCT-GTTGGCAAAG CTGGGCCTTCGACCTAGACACCT-TGTACCCTTGATTAGCTAGAAAGTTCAAGAGATC (SEQ ID NO:17)

S67:
CAGGCATCTGGTGGCCTGAGAATACG-CAATTTGTGGTTACAGAGCACAAGCATG-GCAAGCAGTCTGGCTCACGTGAAAGGT-GAAATCCACGCCAGTGTTTGATGAATTTGATGAT ACAGAACAAACAAATTAGGCTACCCCT-CACCAACCCATCATGGGTCAGGGGCAAG-GATGAATGTGTAGGAATGGCCATCCTTC-TACCAATGTAACCCCATTGTCACTGTTTTCTCAT CCCTTCCTATTAGATTCACTTGGCGCAC-CACCTGCTGCTGGATTCATCTTTC-CAAATCAATGCTTTCATCATCCCTTTC-CCCACTCTCCCACCTGGACTCTGATC (SEQ ID NO:18)

S72:
GATCCACACATGTGTGTAGGCGGGAAAAGGAGCT GGTGGAGCCCCTGAGTATAAAGGGGTGGGAA CTTCTGCTCAGTGGTAAGAGCATAACAGATGGA AGGACAGGTCCTCCTCAGAGCTTGAGGGAAGG AGAAGCAGTTGCTAGCCCTGAAGAATGATTTTG AGCTGGAGAGGAGGGAAGGCACA-GCACAGCCCCGTGTAGTTTAG-AAGCATGTTGGCATACACGATC (SEQ ID NO:19)

S86:
GATCCAAAGGCATAACATAACCTAGAC-CACATGTCCAAACTTTCCTACCAC-CCCACCATCCCTGCCCCAGACAGTC-CCCTCTTGTTCTCTTCCTGATC (SEQ ID NO:20)

S87:
GATCAAAGTCACACAGCCAAGAAG-GAATGGAGGTAGGGTTCCTTCACAATC-CTTGCTGGCCCAGAGC-CCTTTCTCTCTTTTTCTATTTTTTGTGTGTGGCGG GGGTGGGGGTACTGCTTATTAAGAT-GACTGCTTGAGAGGTGAGAGGCAGTTA-CAAAACTGGGAGGATTCCTTGCAGTG-GATTGTACCTCCTTTTCTTTCAGCCCATTCAGTT TAATATTTCCTGAAGAGATC (SEQ ID NO:21)

Southern blot studies using total hepatic DNA from liver disease patients and controls were performed using the PBC RDA products as probes. In addition, PCR studies were performed on hepatic DNA, hepatic cDNA, and serum cDNA derived from patients with end stage liver disease using oligonucleotide primers complementary to the retroviral-like PBC RDA products. The Southern blot and PCR studies confirmed that all the PBC RDA products were encoded in the human genome. Of interest, one of the RDA products (S86) was found to have a significantly increased hybridization signal in PBC patients suggesting a higher copy number of the novel multi-family HERV-like sequence in PBC patients.

Cloning of Exogenous Retrovirus from PBC Patients

In order to maximize the chances of isolating and cloning retroviral cDNA, 2 libraries were made from biliary epithelium cells (BEC) derived from the whole liver of 3 PBC patients undergoing orthotopic liver transplantation and 2 normal livers. The BECs were isolated and cultured with hepatic growth factor for 10 days, when the maximal cell surface AMA reactivity was observed in cells derived from PBC patients (Joplin, R., T. Hishida, H. Tsubouchi, Y. Diakuhara, R. Ayres, J. M. Neuberger, and A. J. Strain. 1992. J Clin Invest. 90:1284–1289). The cDNA synthesized from frozen BECs was cloned into a λ Uni-zap XRTM cDNA library (Stratagene). Using an ex-assist helper phage, the PBC and normal BEC libraries were mass excised from the filamentous bacteriophage vector to the plasmid vector containing each library's cDNA. Isolated virus was also used for our cloning studies. The viral preparations of liver samples were performed to obtain either soluble protein complexes as described by Griffiths et al. (Griffiths et al., 1997. J Virol. 71:2866–2872), or microsomal fractions as described by Garry and colleagues (Garry, R. F., C. D. Fermin, P. F. Kohler, M. L. Market, and H. Luo. 1996. Aids Research and Human Retroviruses. 12:931–940). In addition, viral preparations on bile samples were performed by removing cellular debris, and concentrating the viral pellet from the supernatant in an ultracentrifuge at 100,000 g. Remnant genomic DNA was removed from all the viral preparations with DNAse prior to cDNA synthesis.

In the initial experiments using the mass excised BEC libraries as template, the expected 125 base pair PCR product was observed on the ethidium bromide stained agarose gel derived from the PBC cDNA but not the normal BEC cDNA template. Fifteen separate clones of the PBC PCR product were sequenced and they all shared 97% identity with each other. The blastn search revealed highest homology to HUMREVTRAC, which was defined as a "human reverse transcriptase gene" accession #M25768 deposited by Shih and colleagues in 1989 as one of the sequences detected while screening human peripheral blood mononuclear cells (Shih et al., 1989, J. Virol. 63:64–75). The blastn and blastx searches revealed over 90% homology with murine mammary tumor virus (MMTV) nucleotide and protein sequences. As the sequence encoded the conserved LPQGXXXSP . . . YMDD retroviral reverse transcriptase motifs, it is likely that this gene is retroviral in origin as the serine-proline motif is conserved in all retroviral and hepdnaviral reverse transcriptase proteins. When compared to other known human retroviral nucleotide sequences by ClustalW analysis (MacVector 6.5), the PBC-related retrovirus shared closest sequence homology with HERV-K and HRV-5, B and D type retroviruses (FIG. 3).

In order to confirm these results using a different template, the same degenerate oligonucleotide primers were used in RT-PCR experiments on cDNA from viral preparations of bile and liver tissue. In these studies, approximately 6 to 10 clones of the RT-PCR product were sequenced from each sample. While the PBC-related retroviral sequence was detected in bile (n=5) and liver cDNA (n=2) of all 7 PBC patients studied, approximately 50% to 60% of the clones derived from bile and 80% to 90% of hepatic clones were derived from endogenous retroviruses. In the comparison group of patients without PBC, only one bile sample was positive by RT-PCR for the PBC-related virus in a single bile sample (n=2) and in none of the hepatic samples (n=2) processed in a similar fashion. In the latter study, RT-PCR reactivity was observed in the 1.13 to 1.17 density fraction where enveloped retroviruses co-sediment. From these studies, the PBC-related retrovirus was most frequently encountered in the biliary epithelium of PBC patients, then in bile, but less so in total hepatic tissue. Of note, no previous studies on human or animal retroviruses have been performed in the laboratories where the library construction and subsequent cloning studies were performed. In fact, the sequence variation between the various clones minimizes the concern that these sequences could have arisen as a result of "PCR contamination".

PCR studies were performed to assess the prevalence of the PBC-related retrovirus using total hepatic DNA, hepatic cDNA and serum cDNA. For these studies, PCR oligonucleotide primers and a probe complementary to the PBC-related retrovirus were synthesized and samples from PBC patients, those with other causes of liver disease, patients without parenchymal liver disease, and blood donors were collected. The PCR product was processed on an ethidium bromide stained agarose gel and subsequently detected using Southern blot hybridization to of a PBC-related virus internal oligo probe. Viral sequences were predominantly detected in the hepatic and serum cDNA of patients with PBC (Table 1). The PCR of hepatic DNA was negative in PBC patients and comparison groups consistent with the notion that this sequence is not endogenously encoded. The PBC-related virus cDNA was detected in a significantly higher frequency of PBC liver samples than controls.

These PCR results also reveal that the copy number of this agent is very low or the assays employed to detect the PBC-related virus are not very sensitive. In fact, there is evidence to lend credence to both assumptions. A faint but visible PCR product has only been seen on ethidium bromide stained agarose gel from the PBC BEC cDNA library but not from any patient samples. This finding suggests that the copy number of the virus is far less than one per cell in the liver. Also, considerably more PCR product was observed using the degenerate reverse transcriptase primers with the PBC BEC cDNA library as template as compared to the PBC-related retroviral primers. As all the sequenced clones from the degenerate PCR study of the PBC BEC cDNA library were the PBC-related viral sequence, we believe that the greater signal detected using these primers reflects a greater sensitivity for viral detection compared to the PBC-related primers. Further studies with a nested RT-PCR methodology or real-time PCR methodology will be required to adequately assess the true quantity of the PBC related virus and adequately assess the prevalence of the agent.

TABLE 1

Detection of the PBC-sequence in serum, hepatic and bile cDNA samples by PCR.

| Study groups | Serum cDNA | | Hepatic cDNA* | | Bile cDNA | |
| --- | --- | --- | --- | --- | --- | --- |
| Healthy subjects | 1/22 | (5%) | 0/8 | (0%) | NA | |
| Liver disease | 2/26 | (8%) | 2/29 | (7%) | 10/30 | (33%) |
| PBC | 6/27 | (22%) | 14/49* | (31%) | 9/14 | (64%) |

*p < 0.025 for PBC vs. liver disease controls by Fishers exact test.

Furthermore, there is good evidence to suggest that the PBC-related retrovirus is far less abundant than other known viruses that infect the liver. In electron microscopy studies, viral particles were only visualized in 1:100–300 biliary epithelial cells of PBC patients, supportive of a low abundance infection. Also, in the degenerative PCR cloning studies the detection of the PBC-related virus versus endogenous retroviruses was much higher in total biliary epithelium cDNA than hepatic viral preparations from PBC patients. Therefore, there is no reason to believe that the agent is more abundant in hepatocytes than biliary epithelium. These findings may be analogous to that observed with HRV-5 infection which is an extremely low abundance virus with an estimated copy number of 1 virus per 1,000 cells (Griffiths et al., 1997. J Virol. 71:2866–2872).

Both PBC bile and the PBC BEC cDNA library appeared the best source to clone further genomic material for PBC-related retroviral genome because of the higher abundance of virus in these compartments. In order to isolate more of the viral genome, nested PCR oligonucleotide primers complementary to conserved nucleotide sequences in the MMTV LTR and MMTV pol sequence were synthesized and used for PCR on the PBC BEC cDNA library and random primed bile cDNA. In these studies, a product of the correct size was observed in the PBC BEC cDNA library and 2 of 7 PBC bile samples on ethidium bromide stained agarose gel. Even though the PCR product was not overly abundant, subsequent nested PCR confirmed the presence of a product of the correct molecular weight. The nested product was cloned and sequenced and all clones had the highest score homology with MMTV LTR by blastn search. In addition, conserved oligonucleotide primers complementary to conserved nucleotide sequences of MMTV pol have been used to clone and sequence products with higher score homology with MMTV pol by blastn search.

7. Retrovirus Immunoblot Studies

PBC patients have serum reactivity to HIV and HIAP proteins

In tandem with the cloning experiments, other evidence to implicate a retrovirus in the etiology of PBC was sought. In order to assess whether PBC patients also had evidence of antibody reactivity to retroviral proteins, Western blot studies were conducted using HIV and HIAP immunoblots as surrogate tests for evidence of retrovirus infection (Mason et al., 1998. Lancet. 351:1620–24). In these studies, Western blots were performed using serum samples from 77 PBC patients, 125 liver disease controls, 48 SLE patients and 25 healthy subjects (Mason et al., 1998. Lancet. 351:1620–24). The established criteria for HIV infection was not observed in any patient and no one had reactivity to both HIV gag and envelope proteins. Singular HIV p24 reactivity was observed in a proportion of patients with viral hepatitis, idiopathic biliary disease and SLE, whereas reactivity was seldom observed in healthy controls and patients with genetic or alcohol induced liver disease (Table 2). A significant difference in HIV p24 gag reactivity was observed in the PBC patients versus the control groups with ALD or α-1AT, and the healthy volunteers (p=0.003).

TABLE 2

Frequency of HIV p24 and HIAP immunoblot reactivity in patients with PBC and comparison groups

| | n | HIVp24 | | p* | ≥1 HIAP† | | p* | ≥2 HIAP† | | p* |
|---|---|---|---|---|---|---|---|---|---|---|
| Comparison groups | | | | | | | | | | |
| Healthy | 25 | 1 | (4%) | 0.003 | 2 | (8%) | <0.0001 | 1 | (4%) | <0.0001 |
| ALD or α-AT | 24 | 1 | (4%) | 0.003 | 1 | (4%) | <0.0001 | 0 | | <0.0001 |
| HBV | 43 | 9§ | (60%) | 0.07 | 14 | (33%) | <0.0001 | 5 | (12%) | <0.0001 |
| HCV | 33 | 5§ | (38%) | 0.8 | 19 | (58%) | 0.1 | 10 | (30%) | 0.04 |
| PSC or BA | 23 | 9 | (39%) | 0.42 | 9 | (39%) | 0.002 | 4 | (17%) | 0.004 |
| SLE | 48 | 14 | (29%) | 0.49 | 37 | (77%) | 0.66 | 28 | (58%) | 0.35 |
| PBC | 77 | 27 | (35%) | | 53‡ | (75%) | | 37‡ | (51%) | |

ALD = alcoholic liver disease, α-1AT = α-1 anti-trypsin deficiency, HBV = chronic hepatitis B virus infection, HCV = chronic hepatitis C virus infection, PSC = primary sclerosing cholangitis, BA = biliary atresia, SLE = systemic lupus erythematosus.
*for comparison with PBC by $\chi^2$, †reactivity to ≥1 or ≥2 characterized p17, p24, p30, p46, p60, p80, or p97 HIAP proteins
§data not available for 28 HBV and 20 HCV infected patients.
‡data not available for 6 PBC patients PBC patients have hepatic nucleic acid/protein complexes with hydrodynamic properties of retroviruses In order to address the hypothesis that PBC patients have a hepatic infection with an uncharacterized retrovirus, Western blots were performed using viral extracts from PBC patients and normal liver separated over a 33% to 68% sucrose gradient. The immunoblots were developed with PBC sera and reactivity to 75 kDa and 50 kDa proteins were observed in the samples from all the PBC and normal liver gradients, suggesting autoreactivity to contaminating PDC-E2 and other mitochondrial E2 proteins. However, specific bands at approximately 40 kDa were observed on the Western blots of the PBC microsomal extracts that were not observed in the normal liver gradients. The immunoreactivity was only found in the gradients ranging from 1.14–1.17 g/ml density where enveloped retroviruses co-sediment. Furthermore, RT-PCR studies using the PBC-related retrovirus primers revealed that PBC patients had detectable viral RNA in the 1.14–1.17 g/ml extracts that was not found in the control liver gradients. Thus, only PBC patients' hepatic microsomal extracts contained specific protein/nucleic acid complexes with hydrodynamic properties of enveloped retroviruses, that had both demonstrable antigenic reactivity to PBC patients' sera as well as detectable genomic sequences of the PBC-related retrovirus.

As all the clones derived from the PBC BEC library shared near identity with known MMTV sequences, it seemed likely that the putative PBC virus may share considerable antigenic similarities with MMTV. Accordingly, Western blot studies were performed using the murine MM5MT cells (NCI repository), a MMTV producing breast cancer cell line to determine whether PBC patients had serologic reactivity to the mouse virus. For these studies, crude cell lysates of the MM5MT cells were resolved on a SDS-PAGE gel and polyclonal antibodies to MMTV gag proteins and MMTV pol were used as positive controls (Quality Biotec, NCI repository). Serologic reactivity to multiple proteins were observed in PBC patients that were not observed in controls (FIG. 4). Specifically, the 77 kDa precursor uncleaved gag protein was seen in the majority of PBC patients (arrow head in FIG. 4) and this was a statistically significant finding compared to other patients with liver disease and blood donors (83% vs. 13%; Table 3). In addition, the most PBC patients had serologic reactivity to other proteins correlating to the positive control antibodies as well as proteins at Å 70 kDa, Å 50 kDa and Å 40 kDa but it was difficult to discern whether this reflected antibody reactivity to mitochondrial proteins or viral proteins.

In studies using microsomal extracts from the HIAP infected RH9 lymphoblastoid cells, reactivity to the mitochondrial proteins was not found using specific murine monoclonal antibodies reactive to the PDC-E2 autoantigens. In order to minimize the extraction of mitochondrial proteins, immunoblots were performed using MM5MT microsomal extracts, where the immature nuclear cores of MMTV intracisternal A-type particles are assembled. As a negative control for the microsomal extraction, a non-MMTV producing breast cancer cell line from a Tat-transgenic mouse was used for immunoblots studies to assess whether mitochondrial proteins were being co-purified. In addition to the microsomal extracts, purified viral extracts were used as a substrate for the Western blot studies using a monoclonal MMTV p27 gag antibody as positive control. The MMTV was isolated from milk curd in the stomachs of weanling C3H mice and milk protein was used as a negative control for these studies.

The viral preparations improved the sensitivity and specificity of the immunoblots (FIG. 5). All PBC patients had serologic reactivity to the purified MMTV and 75% of PBC patients had immunoreactivity to the microsomal extracts (Table 3). The predominant reactivity was again observed proteins at approximately 70 kDa, 50 kDa and 40 kDa (arrowheads in FIG. 4 in the microsomal extract blot), however, the specific protein reactivity remains to be determined. In the purified extracts from the weanling stomach, weak serologic reactivity was observed to the precursor 110 gag protein (arrowheads in FIG. 4 in the purified MMTV blot). Whereas, marked reactivity to the 70 kDa protein was observed in all PBC patients studied and approximately half the study group had serologic reactivity to the 50 kDa protein.

Whatever method of extraction was used, the frequency of reactivity to MMTV proteins was significantly greater in the PBC cohort than comparison groups with either chronic hepatitis or blood donors (Table 3). Of note the negative control blots showed no immunoreactivity using PBC serum to either microsomal extracts from the Tat transgenic mouse mammary cancer cell line or the milk blots. The most salient finding from these immunoblot studies is that the majority of PBC patients have serologic reactivity with the murine virus, which is complementary to the RT-PCR detection of the PBC pol sequence in patients with PBC. This suggests that the majority of PBC patients have had exposure to an agent antigenically related to MMTV.

whether PDC-E2 or related host proteins are actually co-packaged with the MMTV particle, as observed in HIV for example, to promote the so called "bystander effect". These studies provide good evidence to suggest that not only do patients with PBC have serologic reactivity to a virus that shares antigenic determinants with MMTV but also MMTV protein complexes harbors antigen(s) that serologically cross react with the major PBC autoantigen, PDC-E2.

TABLE 3

MMTV Western blot studies using purified virus extracted from weanling pup stomachs, and proteins derived from cell lysates and microsomal extracts from the MMTV producing MM5MT cells.

| | MM5MT lysates | | Purified virus | | MM5MT microsomal extracts | | | |
|---|---|---|---|---|---|---|---|---|
| | Study groups | | | | | | | |
| | MMTV p77 gag | | ≥ MMTV proteins | | ≥ MMTV proteins | | ≥ MMTV proteins | |
| Blood Donors | 2/16 | 13% | 0/4 | — | NA | | NA | |
| Liver Disease | 2/15 | 13% | 0/4 | — | 1/59 | 2% | 5/59 | 8% |
| PBC | 29/35** | 83% | 10.10* | 100% | 29/60** | 48% | 45/60** | 75% |

*p = 0.001 and **p <0.001 for PBC vs. liver disease controls and blood donors by Fishers exact test.

The nature of the antigenic proteins providing the serologic reactivity observed in PBC patients has only been partially characterized to date (FIG. 6). Of considerable interest, AMA extracted from sera of PBC patients by elution over an affinity column of purified bovine PDC-E2 (Sigma), also reacted to the 50 kDa and 70 kDa proteins on the Western blots derived from the microsomal extracts and the purified virus (FIG. 6). In contrast, a murine monoclonal antibody raised to bovine PDC-E2 was unreactive with either the microsomal extracts or the purified virus. The AMA immunoblot reactivity to the 70 kDa protein could be blocked by preincubation with 5 mg of bovine PDC-E2, which itself has a molecular weight of approximately 70 kDa. Whereas the serologic reactivity of the eluted human AMA to the 50 kDa protein and the p110 gag precursor were not altered to any great extent by eluting the serum with bovine PDC-E2. Furthermore, preincubation of serum from 3 patients with PBC also had little effect to diminish the immunoreactivity to the purified virus (FIG. 6). These studies suggest that the 50 kDa and 70 kDa proteins that promote the PBC serum reactivity in these blots are unlikely to just represent the mitochondrial autoantigens PDC-X and PDC-E2, which have molecular weights of 50 kDa and 70 kDa, respectively. If this was the case, one would have expected to see immunoreactivity with the murine AMA as well as some demonstrable inhibition of the PBC serum reactivity to the purified MMTV (FIG. 6).

In a previous Western blot study using microsomal extracts of HIAP infected lymphoblastoid cells, no AMA reactivity was observed suggesting that this method of extraction does not co-purify mitochondrial proteins. Also AMA did not react with milk Western blots, so it is likely that the purified MMTV from weanling milk curds were not contaminated with mitochondrial proteins in milk. To date, it has not been assessed whether purified MMTV can block PBC patient serum reactivity to PDC-E2. At this time, it is not known whether this represents "molecular mimicry" with AMA binding to a cross reactive viral protein or 8. Biliary Epithelim Co-Culture and Electron Microscopy Studies PBC patients have a transmissible agent in their lymph nodes It is unknown whether Koch's postulates for infectious disease can be fulfilled for the PBC-related retrovirus because the genetic and environmental factors that influence the development of PBC have not been determined. Furthermore, Koch postulates are difficult to establish for chronic disorders. However, the hypothesis that PBC is an infectious disorder has been tested in vitro using AMA reactivity on biliary epithelium as a phenotypic marker of disease (Sadamoto et al., 1988, Lancet 352:1595–1596). Co-culture studies were conducted with normal BEC extracted from non-liver disease patients and periportal lymph nodes derived from PBC patients and liver disease controls at time of hepatic transplantation. PBC periportal lymph nodes were chosen for the "infected" material as approximately 25% of macrophages in this tissue have AMA reactivity (Sadamoto et al., 1988, Lancet 352:1595–1596). In this study, the lymph nodes were homogenized, diluted in culture medium and incubated with normal BEC for 18 hours. Subsequently, the culture medium was replaced and the cells were maintained for 7 days prior to processing (Sadamoto et al., 1988, Lancet 352:1595–1596).

The BEC protein expression was studied by Western blot and immunohistochemistry using antigen purified AMA. The Western blots revealed a 2 to 3 fold increase in PDC-E2 expression in BEC incubated with PBC lymph node as compared to the comparison group homogenates from other liver disease patients (Sadamoto et al., 1988, Lancet 352:1595–1596). Moreover, the BEC co-cultured with PBC lymph node had demonstrable immunohistochemical reactivity to AMA that was not observed in the comparison group (Sadamoto et al., 1988, Lancet 352:1595–1596). The supernatants from these studies were then used for another set of experiments with fresh BEC that also resulted in AMA reactivity in the new BEC culture when incubated with the PBC derived supernatant. In other words, a transmissible factor from the PBC lymph node transformed normal BEC and after 3 exchanges of culture medium, the supernatant from these cells transformed a second batch of BEC. Thus, it is unlikely that a soluble factor or IgA/PDH-E2 immune complex from the PBC lymph node transformed the second set of BEC, as they would have been diluted considerably by this process.

Figure 7A:
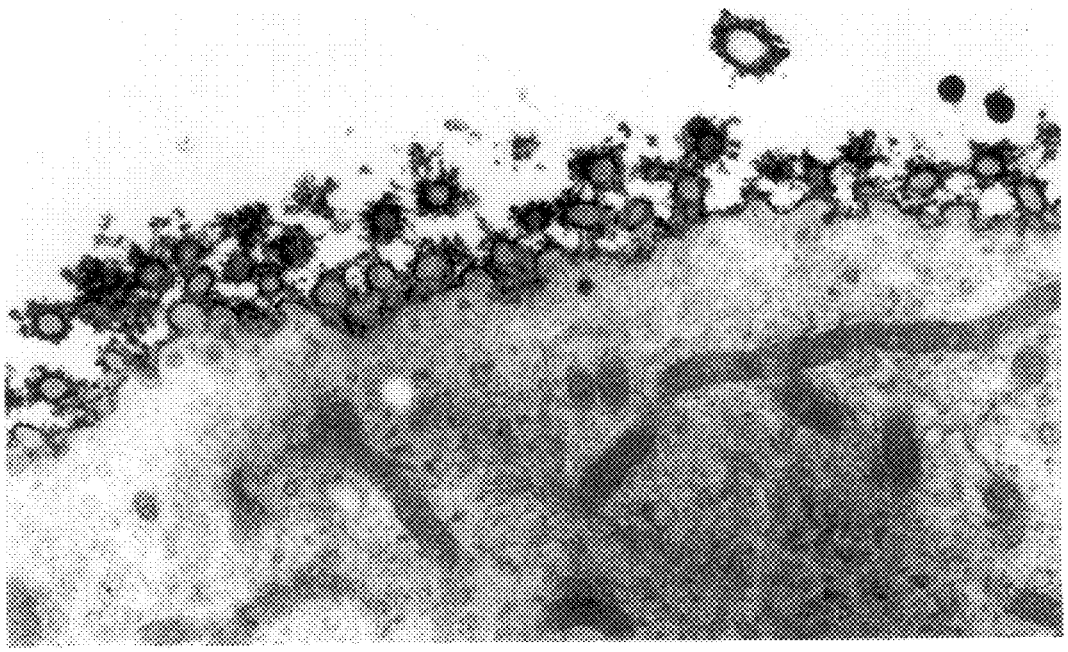
Figure 7B:
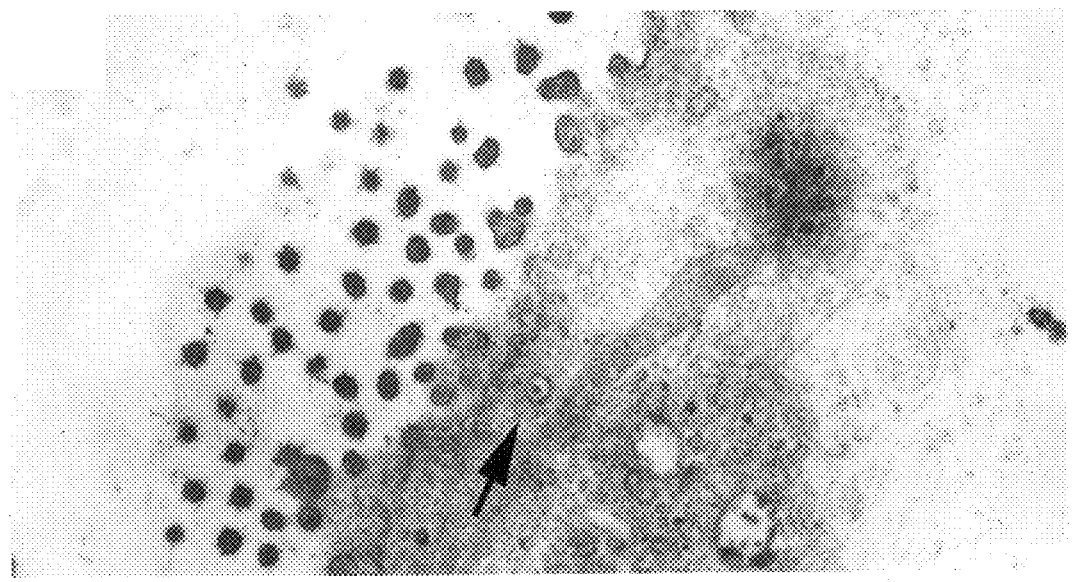

The EM studies were performed after one week after co-culture using BEC prefixed with AMA attached to electromagnetic beads (giving the bulky appearance of the AMA reactivity in FIG. 7a). The AMA bound to the cell surface as well as hollow structures measuring 100 to 150 nm in diameter without the typical nuclear dense core found in mature retroviruses (FIG. 7a). These round structures are too large for microvilli, they do not have the appearance of mature virus and extrastudies will be required to determine whether they are defective viral particles. However a structure resembling an intracisternal A-type particle was observed in an AMA positive BEC near the cell membrane with an 80 to 90 nm nuclear dense structure with a stalk inside a vesicle (arrowed in FIG. 7b).

The spent supernatants from one week old co-culture studies were processed in the ultracentrifuge, negatively stained, and assessed in a blinded fashion by electron microscopy. Virus-like particles were rarely encountered and found only in the PBC co-cultured studies. The particles were 110 to 120 nm in size, spherical in shape and had typical envelop glycoprotein spikes, which were comparable to spikes seen in vivo in BEC derived from PBC patients. In one particle where the negative stain had breached the viral envelope, the core had an eccentrically placed icosohedral nucleus, similar to the appearance of the particles detected in vivo and consistent with classical B-type particle morphology characteristic of MMTV.

The change in phenotype of the normal biliary epithelial cells co-cultured with PBC lymph node homogenates was thought to be secondary to an infection with a transmissible agent. In order to establish whether sequences derived from the putative PBC virus could be detected in biliary epithelial cells, RT-PCR studies were performed in a blinded fashion using nested oligo primers complementary to the putative PBC virus LTR sequence. Total RNA was extracted from 20 coded specimens, including duplicates, of lymph node co-culture studies from 5 patients with PBC, 8 patients with other hepatic disorders and 2 healthy individuals, each sample containing approximately 70,000 to 280,000 cells, which was used for RT-PCR studies. In total 4 of 5 PBC patients and one of 10 controls, with cryptogenic liver disease, were positive for the PBC virus sequence (p=0.017, Fisher's exact test) as judged by visualizing the correct molecular weight band on an ethidium bromide stained agarose gel. Of note, no bands were observed on the first round of PCR suggesting that the sequence was not highly represented. These findings support the hypothesis that the development of AMA reactivity to the PDC-E2 like molecules in the normal biliary epithelial cells is related, in part, to infection with an agent originally cloned from PBC patient's biliary epithelial cells.

TABLE 4

500 μl sucrose gradients of pooled supernatants derived from PBC co-culture studies were assessed for RT activity by the "Silver assay", RT-PCR for the PBC related virus, and density by a refractometer.

| Fraction | Density | RT Activity | PBC virus RT-PCR | Fraction | Density | RT Activity | PBC RT-PCR |
|---|---|---|---|---|---|---|---|
| 1. | 1.0375 | Neg | Neg | 14. | 1.1526 | Pos | Neg |
| 2. | 1.0891 | Neg | Neg | 15. | 1.1553 | Pos | Pos |
| 3. | 1.1209 | Neg | Neg | 16. | 1.1592 | Pos | Neg |
| 4. | 1.1248 | Neg | Neg | 17. | 1.1608 | Neg | Neg |
| 5. | 1.1275 | Neg | Neg | 18. | 1.1659 | Pos | Neg |
| 6. | 1.1309 | Neg | Neg | 19. | 1.1685 | Pos | Pos |
| 7. | 1.1333 | Neg | Neg | 20. | 1.1738 | Neg | Neg |
| 8. | 1.1368 | Neg | Neg | 21. | 1.1778 | Neg | Neg |
| 9. | 1.1386 | Neg | Neg | 22. | 1.1857 | Neg | Neg |
| 10. | 1.1407 | Neg | Neg | 23. | 1.1950 | Neg | Neg |
| 11. | 1.1447 | Neg | Neg | 24. | 1.2003 | Neg | Neg |
| 12. | 1.1473 | Pos | Pos | | | | |
| 13. | 1.1500 | Pos | Neg | Pellet | | Pos | Pos |

In initial RT-PCR experiments on RNA extracted from approximately 5 mls of supernatant of PBC and control lymph node co-culture studies, no product was found using primers complementary to the cloned PBC-related exogenous retrovirus. After it became apparent from the electron microscopy studies (vide infra) that the virus like particles were rarely observed, 56 mls of pooled supernatant from the PBC lymph node co-culture was used to investigate the nature of the virus-like particles. The pooled supernatant was concentrated through a 60% sucrose cushion and then separated through a 20% to 60% gradient. Fractions of 500 μl were collected and the density of each fraction was determined by a refractometer. Reverse transcriptase enzyme reactivity was determined in each fraction by the "Silver assay" (Gross et al., 1998, Science 281:703–706) and RT-PCR was performed on extracted RNA to detect the PBC-related virus. Reverse transcriptase reactivity was detected in 8 gradients ranging from 1.147 to 1.169 g/ml density and 3 of these gradients were RT-PCR positive with primers complementary to the PBC-related retrovirus, (see Table 4 for details). Similar experiments have yet to be performed on the control group's pooled supernatant samples.

Co-culture studies have been performed with liver biopsies derived from PBC patients (n=2) and liver disease controls (n=2) using the SV40 immortalized BEC line. Attempts have been made to infect the lymphoblastoid RH9 cell line with a PBC liver without RT-PCR evidence of infection. Furthermore, the supernatant in vitro sucrose gradient studies have been completed using viral preparations derived from hepatectomy specimens of liver transplant recipients. The PBC pol sequence was detected by RT-PCR in the 1.14–1.17 g/ml fractions of hepatic viral extracts from PBC but not a liver disease control patient. Thus, the PBC patient's hepatic viral preparations contained the specific PBC pol sequence in complexes with hydrodynamic properties of enveloped retroviruses.

Induction of the 'PBC characteristics' can also be induced by conditioned medium: To determine whether there is a factor in the conditioned medium that can also induce the 'PBC characteristics', the 5 day culture medium from BEC pre-incubated either with PBC LN or non-PBC LN ("PBC/non-PBC conditioned media") were inoculated into fresh cultures of BEC from normal subjects. PBC conditioned medium (n=4) resulted in a median induction index of 2.19 (range1.07–3.14) (p<0.04) compared to tissue culture medium alone. Again, the anti-PDC staining pattern was typical of BEC isolated from PBC liver. In contrast, the non-PBC conditioned media (n=4) resulted in an induction index of 1.06 (range 0.93–1.211). Daily sampling of the cells over a seven day period, showed that aberrant E2 expression was first detectable at 4 days after incubations with PBC lymph nodes.

Gamma irradiation abolishes the effect of conditioned medium: Three standard laboratory viruses were used as controls. Herpes simplex virus type I (HSV1) and adenovirus type2 (AV2) contain double stranded DNA; HSV1 is enveloped and AV2 naked. Coxsackie B4 virus (CB4) is an unenveloped virus containing single stranded RNA. The titre of each of the viruses was established by end-point dilution in an appropriate cell line for each virus; HSV 1 in BHK 21 cells, AV2 in 293 cells and CB4 in Vero cells. Each virus stock was irradiated with 30K Gy over a period of 18 hours, and the virus titre re-established. It was found that this level of irradiation treatment led to a near abolition of the replicative potential of the viruses. The same level of irradiation applied to PBC conditioned media (n=7) led to a three fold reduction in the amount of PDC-E2 induced by an aliquot of the non-irradiated conditioned media. Membrane staining of E2 was not seen when BEC were incubated with irradiated PBC-conditioned medium. To test the hypothesis that the irradiation denatured other proteins, the effect of gamma irradiation on the functional effects of TNF-α and IL-1 was examined. Irradiated and non-irradiated aliquots of these media were used to treat cultures of hepatic sinusoidal endothelial cells (HSEC). IL-1 and TNF-α cause the release of IL-1 by HSEC, which was measured in the HSEC supernatants by a specific ELISA. No difference in IL-1 production was observed following irradiation suggesting that the loss of E2 induction following irradiation was due to effects on nucleic acid. However, it remains possible that other soluble molecules may have caused PDC-E2 induction.

The factor(s) responsible for inducing the 'PBC phenotype' may be particulate: In a further attempt to exclude a soluble, non-particulate agent, lymph node homogenates from patients with PBC (n=5) were centrifuged for 80 minutes, and these particle-free supernatants used as inocula in transmission experiments as before. The supernatants did not lead to expression of the PBC 'phenotype' in fresh cells. IgA uptake is not responsible for these effects: Since BECs are able to take up and secrete IgA, IgA has been implicated in the pathogenesis of PBC. It is unlikely that the findings observed in these experiments are consequent on IgA uptake, as no IgA was detected in the supernatants which induced the PBC 'phenotype' (using ELISA with a lower limit of detection 0.3 ng/ml).

Particles, possibly viral, are detectable in the cells and those supernatants that can induce the 'PBC phenotype': Supporting evidence for the involvement of a viral agent was provided by electron microscopy (FIG. 2). In preliminary experiments, virus-like particles were noted in isolated BECs from PBC patients. In further studies, BECs from PBC and non-PBC patients were cultured and thin sections from the cell pellet examined. Virus-like particles were observed of 100–120 nm with a dense, possibly nucleic acid, core. These particles were seen in all three preparations of BEC of PBC origin and only one of 6 preparations of BEC of non-PBC origin. In two further sets of experiments, BEC were exposed to either PBC or non-PBC LN and the cell pellets examined by cell section, while the supernatants were examined by negative staining; again it was shown that there was an association of virus-like particles with PBC-derived inocula (5/9), whether LN or BEC, compared to non-PBC specimens (1/9).

In total, the co-culture studies provide solid evidence that AMA reactivity can be induced in specific fashion in normal biliary epithelium by PBC lymph node and liver homogenates. Moreover, the transmissible agent associated with the transformation of normal BEC to the phenotypic manifestation of PBC has the genomic, morphologic, and hydrodynamic properties of an exogenous B-type retrovirus.

9. Lamivudine Therapy for Patients with Primary Biliary Cirrhosis

Studies have been carried out to assess the efficacy and biologic response of a reverse transcriptase inhibitor in PBC patients using Lamivudine 150 mg per day for one year. Of the 10 patients treated none have had a complete biochemical response to treatment, but 8 patients had a reduction in their serum AMA levels and 2 had no change. It has yet to be assessed whether this fall in AMA reflects a decrease in the biliary autoantigen levels by analyzing AMA immunohistochemistry reactivity on liver biopsies following therapy. Seven patients had adequate pre and post therapy liver biopsies for histologic comparison: 4 patients had diminished hepatic inflammatory index after treatment, 1 had no change, and 2 had histologic progression in their disease. Two patients had a dramatic (>5 decrease in HAI score) histologic improvement associated with a reduction in the Ludwig stage, which has seldom been reported as a spontaneous event.

This anti-viral study has important ramifications for induction of the autoimmune disease process in as much as the hepatic damage in patients with early stages of disease can be markedly reduced with anti-viral therapy alone. Therefore, it is unlikely that the autoimmune phenomena plays a major role in the mediating the disease process in stage I and stage II of PBC. Also, the reduction in AMA is an interesting observation that can not easily be explained. It is possible that reduced levels of AMA may be produced as the disease process resolves, as seen in patients who have a partial hepatic biochemical response to ursodeoxycholic acid. It is also possible that antiviral treatment effects a reduced viral protein/autoantigen expression resulting in a diminished humoral immune response and AMA production.

Immunohistochemistry studies were performed to assess whether Lamivudine therapy has any impact on the aberrant expression of the PDC-E2 like molecules observed on PBC patients' biliary epithelium cells. Immunohistochemistry studies using a murine monoclonal antibody to PDC-E2 was performed on liver biopsy samples from the seven patients with adequate tissues samples pre and post therapy and the results were assessed in a blinded fashion. While 3 patients had detectable AMA staining following 1 year Lamivudine treatment, evidence for the PDC-E2 like molecule had disappeared from 4 patients. The result of this study indicates that the Lamivudine treatment appeared to be associated with histologic improvement as well as diminished autoantigen presentation accompanied by decreased autoantibody levels.

Equivalents

It will be appreciated that the methods and compositions of the present invention are capable of being incorporated in the form of a variety of embodiments, only a few of which have been illustrated and described above. While specific examples have been provided, the above description is illustrative and not restrictive. The invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes that come within the meaning and range of equivalency of the claims are to be embraced within the scope of the invention.

All publications and patent documents cited in this application are incorporated by reference in their entirety for all purposes to the same extent as if each individual publication or patent document were so individually denoted.

What is claimed is:

1. A method for identifying an individual having PBC comprising the step of detecting the presence or absence of PBC retroviral nucleic acid molecule in a sample obtained from the individual wherein a presence of the nucleic acid molecule indicates that the individual has the disorder.

2. The method of claim 1, wherein the nucleic acid molecule has the nucleotide sequence depicted in SEQ ID No. 1, 2, 3, 4, 5, 6, 7, 8, 9, 10, 11, 12, 13, 14, or 15.

3. A composition comprising an isolated PBC retrovirus.

4. A method for identifying an individual infected with a PBC retrovirus comprising the step of detecting the presence or absence of a PBC retroviral nucleic acid molecule in a sample obtained from the individual, wherein a presence of the nucleic acid molecule indicates that the individual is infected with the virus.

5. A method for inhibiting replication of a PBC retrovirus in an individual infected with the virus by administering a composition which targets the PBC pol sequence in a therapeutically effective amount.

6. The method of claim 5 wherein the composition is an antisense molecule.

7. The method of claim 5 wherein the composition is a reverse transcriptase inhibitor or protease inhibitor.

8. A method for identifying the presence of a PBC retrovirus in a tissue sample comprising the step of detecting the presence or absence of immunoreactivity of the sample with a serum specific for PBC, wherein the presence of immunoreactivity indicates that the tissue is infected with the virus.

* * * * *

SEQUENCE LISTING

```
<160> NUMBER OF SEQ ID NOS:  21

<210> SEQ ID NO 1
<211> LENGTH: 160
<212> TYPE: DNA
<213> ORGANISM: Artificial Sequence
<220> FEATURE:
<223> OTHER INFORMATION: Description of Artificial Sequence: Clone 1 Pol

<400> SEQUENCE: 1
taacggccgc cagtgtgctg gaattctgca gattggaagg tgttgccaca gggtatgaaa      60
aatagcccta ctttatgtca aaaatttgta gataaagcta tattgactgt aagggataaa     120
tatcaagact catatatgtg cattacatgg atgacctccc                           160

<210> SEQ ID NO 2
<211> LENGTH: 333
<212> TYPE: DNA
<213> ORGANISM: Artificial Sequence
<220> FEATURE:
<223> OTHER INFORMATION: Description of Artificial Sequence: Clone Pol

<400> SEQUENCE: 2
cccataaggt gaaaggcagt gtagggatca caaagggatg tataatccct gatttatcct      60
catgttgcca gcggagtggc tgactactac gcgccacccc acaggccatg cctaaacctt     120
gaagagaact ttcagtttgg tgaataggcc aattagctgg ccagtctctg cctgctatac     180 aagtttatc tgcccggta tccaagagac cgaggaatct tcttccattc aaggaaatat      240
gaagcatggg tctggaatca cttatttcct gcacccaatg tacatgactt gttgatccga     300
agccttctga gcctcgttct tcctgattac agg                                  333

<210> SEQ ID NO 3
<211> LENGTH: 119
<212> TYPE: DNA
<213> ORGANISM: Artificial Sequence
<220> FEATURE:
<223> OTHER INFORMATION: Description of Artificial Sequence: Clone
      T-CI-26 pol

<400> SEQUENCE: 3
ttgccacagg gtatgaaaaa tagccctact ttatgtcaaa aatttgtaga taaagctata      60
ttgactgtaa gggataaata tcaagactca tatatgtgca ttacatggat gacctccca     119

<210> SEQ ID NO 4
```

<211> LENGTH: 146
<212> TYPE: DNA
<213> ORGANISM: Artificial Sequence
<220> FEATURE:
<223> OTHER INFORMATION: Description of Artificial Sequence: T-CI-31 pol

<400> SEQUENCE: 4
gtgctgcccc agggtatgaa aaatagccct actttatgtc aaaaatttgt agataaagct    60
atattgactg taagggataa atatcaagac tcatatatgt gcattacatg gatgacctaa   120
gggcgaattc cagcacactg cgccgt                                        146

<210> SEQ ID NO 5
<211> LENGTH: 114
<212> TYPE: DNA
<213> ORGANISM: Artificial Sequence
<220> FEATURE:
<223> OTHER INFORMATION: Description of Artificial Sequence: Clone
      T-CI-30 pol

<400> SEQUENCE: 5
gttgccccag ggtatggaaa aatagcccta ctttatgtca aaatttgta gataaagcta     60 tatagactgt aagggataaa tatcaagact catatatgtg cattacatgg atga          114

<210> SEQ ID NO 6
<211> LENGTH: 119
<212> TYPE: DNA
<213> ORGANISM: Artificial Sequence
<220> FEATURE:
<223> OTHER INFORMATION: Description of Artificial Sequence: Clone
      T-CI-29 pol

<400> SEQUENCE: 6
gctaccacaa ggtatgaaaa atagccctac tttatgtcaa aaatttgtag ataaagctat    60
attgactgta agggataaat atcaagactc atatatgtgc attacatgga tgacatccc    119

<210> SEQ ID NO 7
<211> LENGTH: 117
<212> TYPE: DNA
<213> ORGANISM: Artificial Sequence
<220> FEATURE:
<223> OTHER INFORMATION: Description of Artificial Sequence: Clone
      T-CI-28 pol

<400> SEQUENCE: 7
gttaccacag ggtatgaaaa atagccctac tttatgtcaa aaatttgtag ataaagctat    60
atgactgtaa gggataaata tcaagactca tatatgtgmt tacatgrtag actccca      117

<210> SEQ ID NO 8
<211> LENGTH: 143
<212> TYPE: DNA
<213> ORGANISM: Artificial Sequence
<220> FEATURE:
<223> OTHER INFORMATION: Description of Artificial Sequence: Clone
      T-CI-27 pol

<400> SEQUENCE: 8
ctgccacaag gtagggaggt catccatgta atgcacaata tatgagtctt gatatttatc    60
ccttacagtc aatatagctt tatctacaaa ttttttgacat aaagtagggc tattttttcat  120 accctgtggc agcaccttcc aaa                                           143

<210> SEQ ID NO 9
<211> LENGTH: 139

```
<212> TYPE: DNA
<213> ORGANISM: Artificial Sequence
<220> FEATURE:
<223> OTHER INFORMATION: Description of Artificial Sequence: Clone
      Es60-7/GO16LTR

<400> SEQUENCE: 9
acagaagagc tattaaaaga gtcaagggtg agagccctgc gagcacgaac cgcaacttcc    60
cccaatagcc ccaggcaaag cagagctatg ccaagtttgc agcagagaat gaatatgtct   120
ttatctgatg ggctcatcc                                                139

<210> SEQ ID NO 10
<211> LENGTH: 138
<212> TYPE: DNA
<213> ORGANISM: Artificial Sequence
<220> FEATURE:
<223> OTHER INFORMATION: Description of Artificial Sequence: Clone
      Es60-6/GO16LTR

<400> SEQUENCE: 10
acagaagagc tattaaaaga gtcaagggtg agagccctgc gagcacgaac cgcaacttcc    60
cccaatagcc ccaggcaaag cagagctatg ccaagtttgc agcagagaat gaatatgtct   120
ttatctgatg ggctcatc                                                 138

<210> SEQ ID NO 11
<211> LENGTH: 146
<212> TYPE: DNA
<213> ORGANISM: Artificial Sequence
<220> FEATURE:
<223> OTHER INFORMATION: Description of Artificial Sequence: Clone
      Es60-5/GO16LTR

<400> SEQUENCE: 11
tgagcccatc agacaaagac atattcattc tctgctgcaa acttggcata gctctgcttt    60
gcctggggct attgggggaa gttgcggttc gtgctcgcag ggctctcacc cttgactctt   120
ttaatagctc ttctgtgcaa gattac                                        146

<210> SEQ ID NO 12
<211> LENGTH: 146
<212> TYPE: DNA
<213> ORGANISM: Artificial Sequence
<220> FEATURE:
<223> OTHER INFORMATION: Description of Artificial Sequence: Clone
      Es60-4/GO16LTR

<400> SEQUENCE: 12
tgagcccatc agacaaagac atattcattc tctgctgcaa acttggcata gctctgcttt    60
gcctggggct attgggggaa gttgcggttc gtgctcgcag ggctctcacc cttgactctt   120
ttaatagctc ttctgtgcaa gattac                                        146

<210> SEQ ID NO 13
<211> LENGTH: 152
<212> TYPE: DNA
<213> ORGANISM: Artificial Sequence
<220> FEATURE:
<223> OTHER INFORMATION: Description of Artificial Sequence: Clone
      Es60-3/GO16LTR

<400> SEQUENCE: 13
gccagtgtga tggatatctg cagaattcgc ccttttgttt cccaccaagg acgacccgtc    60
tgcgcacaaa cggatgagcc catcagacaa agacatatca ttctctgctg caaacttggc   120
```

```
atagctctgc tttgcctggg gctattgggg ga                                    152

<210> SEQ ID NO 14
<211> LENGTH: 140
<212> TYPE: DNA
<213> ORGANISM: Artificial Sequence
<220> FEATURE:
<223> OTHER INFORMATION: Description of Artificial Sequence: Clone
      Es60-2/GO16LTR

<400> SEQUENCE: 14
acagaagagc tattaaaaga gtcaagggtg agagccccgc gagcacgaac cgcaacttcc       60
cccaatagcc ccaggcaaag cagagctatg ccaagtttgc agcagagaat gaatatgtct      120
ttgtctgatg ggctcatccg                                                  140

<210> SEQ ID NO 15
<211> LENGTH: 95
<212> TYPE: DNA
<213> ORGANISM: Artificial Sequence
<220> FEATURE:
<223> OTHER INFORMATION: Description of Artificial Sequence: Clone
      Es60-1/GO16LTR

<400> SEQUENCE: 15
cgccagtgtg atggatatct gcagaattcg cccttatgtt tcccaccaag gacgacccgt       60
ttgcgcacaa acgatgagcc catcagacaa agaca                                  95

<210> SEQ ID NO 16
<211> LENGTH: 236
<212> TYPE: DNA
<213> ORGANISM: Artificial Sequence
<220> FEATURE:
<223> OTHER INFORMATION: Description of Artificial Sequence: RDA
      product S139
<221> NAME/KEY: modified_base
<222> LOCATION: 1...236
<223> OTHER INFORMATION: n=a, c, g, or t

<400> SEQUENCE: 16
gatcctgtcc gtgatgccaa ttgtcaggtt ctaacaggtc tgaggggagt cggntgagca       60
agtggcgagt ggctggaaaa acgctggagg aatcgcagac agtttcaata tggcnttact      120
cactatctgg gtgtgagtga gactgggcat cagncatatg tacagcttta snaggntaac      180
tatatgnttt atagataata gtngcttgag ccaagcacga gctcatgtgt gtgatc          236

<210> SEQ ID NO 17
<211> LENGTH: 217
<212> TYPE: DNA
<213> ORGANISM: Artificial Sequence
<220> FEATURE:
<223> OTHER INFORMATION: Description of Artificial Sequence: RDA product
      S59

<400> SEQUENCE: 17
gatcgtagtt ggcaaaagcc tgtgattcca aggaacctcc acaactgttt taatgtctta       60
ggtcgaggat aagccggtat aggttgtatt cattctcgct aagagccctg gtccctctgg      120
ctaagattag gcctagatat ttgacctgct gttggcaaag ctgggccttc gacctagaca      180
ccttgtaccc ttgattagct agaaagttca agagatc                               217

<210> SEQ ID NO 18
<211> LENGTH: 337
```

<212> TYPE: DNA
<213> ORGANISM: Artificial Sequence
<220> FEATURE:
<223> OTHER INFORMATION: Description of Artificial Sequence: RDA product S67

<400> SEQUENCE: 18

```
caggcatctg gtggcctgag aatacgcaat ttgtggttac agagcacaag catggcaagc      60
agtctggctc acgtgaaagg tgaaatccac gccagtgttt gatgaatttg atgatacaga    120
acaaacaaat taggctaccc ctcaccaacc catcatgggt caggggcaag gatgaatgtg    180
taggaatggc catccttcta ccaatgtaac cccattgtca ctgttttctc atcccttcct    240
attagattca cttggcgcac cacctgctgc tggattcatc tttccaaatc aatgctttca    300
tcatcccttt ccccactctc ccacctggac tctgatc                             337
```

<210> SEQ ID NO 19
<211> LENGTH: 229
<212> TYPE: DNA
<213> ORGANISM: Artificial Sequence
<220> FEATURE:
<223> OTHER INFORMATION: Description of Artificial Sequence: RDA product S72

<400> SEQUENCE: 19

```
gatccacaca tgtgtgtagg cgggaaaagg agctggtgga gccctgagt ataaaggggt       60
gggaacttct gctcagtggt aagagcataa cagatggaag gacaggtcct cctcagagct    120
tgagggaagg agaagcagtt gctagccctg aagaatgatt ttgagctgga gaggagggaa    180
ggcacagcac agccccgtgt agtttagaag catgttggca tacacgatc                229
```

<210> SEQ ID NO 20
<211> LENGTH: 98
<212> TYPE: DNA
<213> ORGANISM: Artificial Sequence
<220> FEATURE:
<223> OTHER INFORMATION: Description of Artificial Sequence: RDA product S86

<400> SEQUENCE: 20

```
gatccaaagg cataacataa cctagaccac atgtccaaac tttcctacca ccccaccatc      60
cctgccccag acagtcccct cttgttctct tcctgatc                             98
```

<210> SEQ ID NO 21
<211> LENGTH: 235
<212> TYPE: DNA
<213> ORGANISM: Artificial Sequence
<220> FEATURE:
<223> OTHER INFORMATION: Description of Artificial Sequence: RDA product S87

<400> SEQUENCE: 21

```
gatcaaagtc acacagccaa gaaggaatgg aggtagggtt ccttcacaat ccttgctggc      60
cccagagccc tttctctctt tttctatttt ttgtgtgtgg cgggggtggg ggtactgctt    120
attaagatga ctgcttgaga ggtgagaggc agttacaaaa ctgggaggat tccttgcagt    180
ggattgtacc tccttttctt tcagcccatt cagtttaata tttcctgaag agatc          235
```